(12) United States Patent
Rowe et al.

(10) Patent No.: US 8,184,873 B2
(45) Date of Patent: *May 22, 2012

(54) WHITE-LIGHT SPECTRAL BIOMETRIC SENSORS

(75) Inventors: Robert K. Rowe, Corrales, NM (US); Stephen P. Corcoran, Corrales, NM (US); Kristin A. Nixon, Albuquerque, NM (US); Todd Doucet, Albuquerque, NM (US); Ryan Martin, Albuquerque, NM (US)

(73) Assignee: Lumidigm, Inc., Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/815,196

(22) Filed: Jun. 14, 2010

(65) Prior Publication Data

US 2011/0310236 A1    Dec. 22, 2011

Related U.S. Application Data

(63) Continuation of application No. 11/458,607, filed on Jul. 19, 2006, now Pat. No. 7,751,594, which is a continuation-in-part of application No. 10/818,698, filed on Apr. 5, 2004, now Pat. No. 7,147,153, said application No. 11/458,607 is a continuation-in-part of application No. 11/219,006, filed on Sep. 1, 2005, now Pat. No. 7,668,350, which is a continuation-in-part of application No. 10/818,698, filed on Apr. 5, 2004, now Pat. No. 7,147,153, said application No. 11/458,607 is a continuation-in-part of application No. 11/115,100, filed on Apr. 25, 2005, now Pat. No. 7,460,696, said application No. 11/458,607 is a continuation-in-part of application No. 11/115,101, filed on Apr. 25, 2005, now Pat. No. 7,394,919, said application No. 11/458,607 is a continuation-in-part of application No. 11/115,075, filed on Apr. 25, 2005, now Pat. No. 7,539,330.

(60) Provisional application No. 60/460,247, filed on Apr. 4, 2003, provisional application No. 60/483,281, filed on Jun. 27, 2003, provisional application No. 60/504,594, filed on Sep. 18, 2003, provisional application No. 60/552,662, filed on Mar. 10, 2004, provisional application No. 60/576,364, filed on Jun. 1, 2004, provisional application No. 60/600,867, filed on Aug. 11, 2004, provisional application No. 60/610,802, filed on Sep. 17, 2004, provisional application No. 60/654,354, filed on Feb. 18, 2005, provisional application No. 60/659,024, filed on Mar. 4, 2005.

(51) Int. Cl.
*G06K 9/00* (2006.01)
(52) U.S. Cl. ........................ 382/124; 340/5.53; 340/5.83
(58) Field of Classification Search .................. 382/124; 340/5.53, 5.83
See application file for complete search history.

(56) References Cited

U.S. PATENT DOCUMENTS 3,508,830 A    4/1970  Hopkins et al.
(Continued)

FOREIGN PATENT DOCUMENTS

CN    1307711 A    8/2001
(Continued)

OTHER PUBLICATIONS

Anderson, C. E. et al., "Fundamentals of Calibration Transfer Through Procrustes Analysis," Appln. Spectros., vol. 53, No. 10 (1999) p. 1268-1276.
(Continued)

*Primary Examiner* — John Strege
(74) *Attorney, Agent, or Firm* — Marsh Fischmann & Breyfogle LLP

(57) ABSTRACT

Methods and systems are provided for performing a biometric function. A purported skin site of an individual is illuminated with white light. Light scattered from the purported skin site is received with a color imager on which the received light is incident. Spatially distributed images of the purported skin site are derived and correspond to different volumes of illuminated tissue of the individual. The images are analyzed to perform the biometric function.

26 Claims, 11 Drawing Sheets

U.S. PATENT DOCUMENTS

| | | |
|---|---|---|
| 3,619,060 A | 11/1971 | Johnson |
| 3,854,319 A | 12/1974 | Burroughs et al. |
| 3,872,443 A | 3/1975 | Ott |
| 3,910,701 A | 10/1975 | Henderson et al. |
| RE29,008 E | 10/1976 | Ott |
| 4,035,083 A | 7/1977 | Woodriff et al. |
| 4,142,797 A | 3/1979 | Astheimer |
| 4,169,676 A | 10/1979 | Kaiser |
| 4,170,987 A | 10/1979 | Anselmo et al. |
| 4,260,220 A | 4/1981 | Whitehead |
| 4,322,163 A | 3/1982 | Schiller |
| 4,427,889 A | 1/1984 | Muller |
| 4,537,484 A | 8/1985 | Fowler |
| 4,598,715 A | 7/1986 | Machler et al. |
| 4,653,880 A | 3/1987 | Sting et al. |
| 4,654,530 A | 3/1987 | Dybwad |
| 4,655,225 A | 4/1987 | Dahne et al. |
| 4,656,562 A | 4/1987 | Sugino |
| 4,657,397 A | 4/1987 | Oehler et al. |
| 4,661,706 A | 4/1987 | Messerschmidt et al. |
| 4,684,255 A | 8/1987 | Ford |
| 4,699,149 A | 10/1987 | Rice |
| 4,712,912 A | 12/1987 | Messerschmidt |
| 4,730,882 A | 3/1988 | Messerschmidt |
| 4,747,147 A | 5/1988 | Sparrow |
| 4,787,013 A | 11/1988 | Sugino et al. |
| 4,787,708 A | 11/1988 | Whitehead |
| 4,830,496 A | 5/1989 | Young |
| 4,853,542 A | 8/1989 | Milosevic et al. |
| 4,857,735 A | 8/1989 | Noller |
| 4,859,064 A | 8/1989 | Messerschmidt et al. |
| 4,866,644 A | 9/1989 | Shenk et al. |
| 4,867,557 A | 9/1989 | Takatani et al. |
| 4,882,492 A | 11/1989 | Schlager |
| 4,883,953 A | 11/1989 | Koashi et al. |
| 4,936,680 A | 6/1990 | Henkes et al. |
| 4,937,764 A | 6/1990 | Komatsu et al. |
| 4,944,021 A | 7/1990 | Hoshino et al. |
| 4,975,581 A | 12/1990 | Robinson et al. |
| 5,015,100 A | 5/1991 | Doyle |
| 5,019,715 A | 5/1991 | Sting et al. |
| 5,028,787 A | 7/1991 | Rosenthal et al. |
| 5,051,602 A | 9/1991 | Sting et al. |
| 5,055,658 A | 10/1991 | Cockburn |
| 5,068,536 A | 11/1991 | Rosenthal |
| 5,070,874 A | 12/1991 | Barnes et al. |
| 5,077,803 A | 12/1991 | Kato et al. |
| 5,088,817 A | 2/1992 | Igaki et al. |
| 5,109,428 A | 4/1992 | Igaki et al. |
| 5,146,102 A | 9/1992 | Higuchi et al. |
| 5,158,082 A | 10/1992 | Jones |
| 5,163,094 A | 11/1992 | Prokoski et al. |
| 5,177,802 A | 1/1993 | Fujimoto et al. |
| 5,178,142 A | 1/1993 | Harjunmaa et al. |
| 5,179,951 A | 1/1993 | Knudson |
| 5,204,532 A | 4/1993 | Rosenthal |
| 5,222,495 A | 6/1993 | Clarke et al. |
| 5,222,496 A | 6/1993 | Clarke et al. |
| 5,223,715 A | 6/1993 | Taylor |
| 5,225,678 A | 7/1993 | Messerschmidt |
| 5,230,702 A | 7/1993 | Lindsay et al. |
| 5,237,178 A | 8/1993 | Rosenthal et al. |
| 5,243,546 A | 9/1993 | Maggard |
| 5,257,086 A | 10/1993 | Fateley et al. |
| 5,258,922 A | 11/1993 | Grill |
| 5,267,152 A | 11/1993 | Yang et al. |
| 5,268,749 A | 12/1993 | Weber et al. |
| 5,291,560 A | 3/1994 | Daugman |
| 5,299,570 A | 4/1994 | Hatschek |
| 5,303,026 A | 4/1994 | Strobl et al. |
| 5,311,021 A | 5/1994 | Messerschmidt |
| 5,313,941 A | 5/1994 | Braig et al. |
| 5,321,265 A | 6/1994 | Block |
| 5,331,958 A | 7/1994 | Oppenheimer |
| 5,335,288 A | 8/1994 | Faulkner |
| 5,348,003 A | 9/1994 | Caro |
| 5,351,686 A | 10/1994 | Steuer et al. |
| 5,355,880 A | 10/1994 | Thomas et al. |
| 5,360,004 A | 11/1994 | Purdy et al. |
| 5,361,758 A | 11/1994 | Hall et al. |
| 5,366,903 A | 11/1994 | Lundsgaard et al. |
| 5,372,135 A | 12/1994 | Mendelson et al. |
| 5,379,764 A | 1/1995 | Barnes et al. |
| 5,402,778 A | 4/1995 | Chance |
| 5,405,315 A | 4/1995 | Khuri et al. |
| 5,413,096 A | 5/1995 | Hart |
| 5,413,098 A | 5/1995 | Benaron et al. |
| 5,419,321 A | 5/1995 | Evans |
| 5,435,309 A | 7/1995 | Thomas et al. |
| 5,441,053 A | 8/1995 | Lodder et al. |
| 5,452,723 A | 9/1995 | Wu et al. |
| 5,459,317 A | 10/1995 | Small et al. |
| 5,459,677 A | 10/1995 | Kowalski et al. |
| 5,460,177 A | 10/1995 | Purdy et al. |
| 5,483,335 A | 1/1996 | Tobias |
| 5,494,032 A | 2/1996 | Robinson et al. |
| 5,505,726 A | 4/1996 | Meserol |
| 5,507,723 A | 4/1996 | Keshaviah |
| 5,515,847 A | 5/1996 | Braig et al. |
| 5,518,623 A | 5/1996 | Keshaviah et al. |
| 5,523,054 A | 6/1996 | Switalski et al. |
| 5,533,509 A | 7/1996 | Koashi et al. |
| 5,537,208 A | 7/1996 | Bertram et al. |
| 5,539,207 A | 7/1996 | Wong et al. |
| 5,552,997 A | 9/1996 | Massart |
| 5,559,504 A | 9/1996 | Itsumi et al. |
| 5,568,251 A | 10/1996 | Davies et al. |
| 5,596,992 A | 1/1997 | Haaland et al. |
| 5,606,164 A | 2/1997 | Price et al. |
| 5,613,014 A | 3/1997 | Eshera et al. |
| 5,630,413 A | 5/1997 | Thomas et al. |
| 5,636,633 A | 6/1997 | Messerschmidt et al. |
| 5,655,530 A | 8/1997 | Messerschmidt |
| 5,672,864 A | 9/1997 | Kaplan |
| 5,672,875 A | 9/1997 | Block et al. |
| 5,677,762 A | 10/1997 | Ortyn et al. |
| 5,681,273 A | 10/1997 | Brown |
| 5,708,593 A | 1/1998 | Saby et al. |
| 5,719,399 A | 2/1998 | Alfano et al. |
| 5,719,950 A | 2/1998 | Osten et al. |
| 5,724,268 A | 3/1998 | Sodickson et al. |
| 5,729,619 A | 3/1998 | Puma |
| 5,743,262 A | 4/1998 | Lepper, Jr. et al. |
| 5,747,806 A | 5/1998 | Khalil |
| 5,750,994 A | 5/1998 | Schlager |
| 5,751,835 A | 5/1998 | Topping et al. |
| 5,751,836 A | 5/1998 | Wildes et al. |
| 5,761,330 A | 6/1998 | Stoianov et al. |
| 5,782,755 A | 7/1998 | Chance et al. |
| 5,737,439 A | 8/1998 | Lapsley et al. |
| 5,792,050 A | 8/1998 | Alam et al. |
| 5,792,053 A | 8/1998 | Skladnev et al. |
| 5,793,881 A | 8/1998 | Stiver et al. |
| 5,796,858 A | 8/1998 | Zhou et al. |
| 5,808,739 A | 9/1998 | Turner et al. |
| 5,818,048 A | 10/1998 | Sodickson et al. |
| 5,823,951 A | 10/1998 | Messerschmidt et al. |
| 5,828,066 A | 10/1998 | Messerschmidt |
| 5,830,132 A | 11/1998 | Robinson |
| 5,830,133 A | 11/1998 | Osten et al. |
| 5,850,623 A | 12/1998 | Carman, Jr. et al. |
| 5,853,370 A | 12/1998 | Chance et al. |
| 5,857,462 A | 1/1999 | Thomas et al. |
| 5,859,420 A | 1/1999 | Borza |
| 5,860,421 A | 1/1999 | Eppstein et al. |
| 5,867,265 A | 2/1999 | Thomas |
| 5,886,347 A | 3/1999 | Inoue et al. |
| 5,902,033 A | 5/1999 | Levis et al. |
| 5,914,780 A | 6/1999 | Turner et al. |
| 5,929,443 A | 7/1999 | Alfano et al. |
| 5,933,792 A | 8/1999 | Andersan et al. |
| 5,935,062 A | 8/1999 | Messerschmidt et al. |
| 5,945,676 A | 8/1999 | Khalil |
| 5,949,543 A | 9/1999 | Bleier et al. |
| 5,957,841 A | 9/1999 | Maruo et al. |
| 5,961,449 A | 10/1999 | Toida et al. |
| 5,963,319 A | 10/1999 | Jarvis et al. |

| | | | | | | |
|---|---|---|---|---|---|---|
| 5,978,495 | A | 11/1999 | Thomopoulos et al. | 6,574,490 B2 | 6/2003 | Abbink et al. |
| 5,987,346 | A | 11/1999 | Benaron et al. | 6,597,945 B2 | 7/2003 | Marksteiner |
| 5,999,637 | A | 12/1999 | Toyoda et al. | 6,606,509 B2 | 8/2003 | Schmitt |
| 6,005,722 | A | 12/1999 | Butterworth et al. | 6,628,809 B1 | 9/2003 | Rowe et al. |
| 6,016,435 | A | 1/2000 | Maruo et al. | 6,631,199 B1 | 10/2003 | Topping et al. |
| 6,025,597 | A | 2/2000 | Sterling et al. | 6,741,729 B2 | 5/2004 | Bjorn et al. |
| 6,026,314 | A | 2/2000 | Amerov et al. | 6,749,115 B2 | 6/2004 | Gressel et al. |
| 6,028,773 | A | 2/2000 | Hundt | 6,799,275 B1 | 9/2004 | Bjorn |
| 6,031,609 | A | 2/2000 | Funk et al. | 6,799,726 B2 | 10/2004 | Stockhammer |
| 6,034,370 | A | 3/2000 | Messerschmidt | 6,816,605 B2 | 11/2004 | Rowe et al. |
| 6,040,578 | A | 3/2000 | Malin et al. | 6,825,930 B2 | 11/2004 | Cronin et al. |
| 6,041,247 | A | 3/2000 | Weckstrom et al. | 6,853,444 B2 | 2/2005 | Haddad |
| 6,041,410 | A | 3/2000 | Hsu et al. | 6,898,299 B1 | 5/2005 | Brooks |
| 6,043,492 | A | 3/2000 | Lee et al. | 6,928,181 B2 | 8/2005 | Brooks |
| 6,044,285 | A | 3/2000 | Chaiken et al. | 6,937,885 B1 | 8/2005 | Lewis et al. |
| 6,045,502 | A | 4/2000 | Eppstein et al. | 6,958,194 B1 | 10/2005 | Hopper et al. |
| 6,046,808 | A | 4/2000 | Fateley | 6,995,384 B2 | 2/2006 | Lee et al. |
| 6,049,727 | A | 4/2000 | Crothall | 7,047,419 B2 | 5/2006 | Black |
| 6,056,738 | A | 5/2000 | Marchitto et al. | 7,084,415 B2 | 8/2006 | Iwai |
| 6,057,925 | A | 5/2000 | Anthon | 7,147,153 B2 * | 12/2006 | Rowe et al. .................. 235/382 |
| 6,061,581 | A | 5/2000 | Alam et al. | 7,254,255 B2 | 8/2007 | Dennis |
| 6,061,582 | A | 5/2000 | Small et al. | 7,263,213 B2 | 8/2007 | Rowe |
| 6,066,847 | A | 5/2000 | Rosenthal | 7,287,013 B2 | 10/2007 | Schneider et al. |
| 6,069,689 | A | 5/2000 | Zeng et al. | 7,347,365 B2 | 3/2008 | Rowe |
| 6,070,093 | A | 5/2000 | Oosta et al. | 7,366,331 B2 | 4/2008 | Higuchi |
| 6,073,037 | A | 6/2000 | Alam et al. | 7,386,152 B2 | 6/2008 | Rowe et al. |
| 6,081,612 | A | 6/2000 | Gutkowicz-Krusin et al. | 7,394,919 B2 | 7/2008 | Rowe et al. |
| 6,088,605 | A | 7/2000 | Griffith et al. | 7,397,943 B2 | 7/2008 | Merbach et al. |
| 6,088,607 | A | 7/2000 | Diab et al. | 7,440,597 B2 | 10/2008 | Rowe |
| 6,097,035 | A | 8/2000 | Belongie et al. | 7,460,696 B2 | 12/2008 | Rowe |
| 6,100,811 | A | 8/2000 | Hsu et al. | 7,508,965 B2 | 3/2009 | Rowe et al. |
| 6,115,484 | A | 9/2000 | Bowker et al. | 7,515,252 B2 | 4/2009 | Hernandez |
| 6,115,673 | A | 9/2000 | Malin et al. | 7,539,330 B2 | 5/2009 | Rowe |
| 6,122,042 | A | 9/2000 | Wunderman et al. | 7,545,963 B2 | 6/2009 | Rowe |
| 6,122,394 | A | 9/2000 | Neukermans et al. | 7,627,151 B2 | 12/2009 | Rowe |
| 6,122,737 | A | 9/2000 | Bjorn et al. | 7,668,350 B2 | 2/2010 | Rowe |
| 6,125,192 | A | 9/2000 | Bjorn et al. | 7,735,729 B2 | 6/2010 | Rowe |
| 6,141,101 | A | 10/2000 | Bleier et al. | 7,751,594 B2 * | 7/2010 | Rowe et al. .................. 382/115 |
| 6,147,749 | A | 11/2000 | Kubo et al. | 7,801,338 B2 | 9/2010 | Rowe |
| 6,148,094 | A | 11/2000 | Kinsella | 7,801,339 B2 | 9/2010 | Sidlauskas et al. |
| 6,152,876 | A | 11/2000 | Robinson et al. | 7,804,984 B2 | 9/2010 | Sidlauskas et al. |
| 6,154,658 | A | 11/2000 | Caci | 7,819,311 B2 | 10/2010 | Rowe et al. |
| 6,157,041 | A | 12/2000 | Thomas et al. | 7,831,072 B2 | 11/2010 | Rowe |
| 6,159,147 | A | 12/2000 | Lichter et al. | 7,835,554 B2 | 11/2010 | Rowe |
| 6,172,743 | B1 | 1/2001 | Kley et al. | 7,899,217 B2 | 3/2011 | Uludag et al. |
| 6,175,407 | B1 | 1/2001 | Sartor | 7,995,808 B2 * | 8/2011 | Rowe et al. .................. 382/124 |
| 6,181,414 | B1 | 1/2001 | Raz et al. | 2002/0009213 A1 | 1/2002 | Rowe et al. |
| 6,181,958 | B1 | 1/2001 | Steuer et al. | 2002/0065468 A1 | 5/2002 | Utzinger et al. |
| 6,188,781 | B1 | 2/2001 | Brownlee | 2002/0101566 A1 | 8/2002 | Elsner et al. |
| 6,193,153 | B1 | 2/2001 | Lambert | 2002/0111546 A1 | 8/2002 | Cook et al. |
| 6,208,749 | B1 | 3/2001 | Gutkowicz-Krusin | 2002/0138768 A1 | 9/2002 | Murakami et al. |
| 6,212,424 | B1 | 4/2001 | Robinson | 2002/0171834 A1 | 11/2002 | Rowe et al. |
| 6,226,541 | B1 | 5/2001 | Eppstein et al. | 2002/0183624 A1 | 12/2002 | Rowe et al. |
| 6,229,908 | B1 | 5/2001 | Edmonds et al. | 2003/0025897 A1 | 2/2003 | Iwai |
| 6,230,034 | B1 | 5/2001 | Messerschmidt et al. | 2003/0044051 A1 | 3/2003 | Fujieda |
| 6,236,047 | B1 | 5/2001 | Malin et al. | 2003/0078504 A1 | 4/2003 | Rowe |
| 6,240,306 | B1 | 5/2001 | Rohrscheib et al. | 2003/0095525 A1 | 5/2003 | Lavin et al. |
| 6,240,309 | B1 | 5/2001 | Yamashita et al. | 2003/0128867 A1 | 7/2003 | Bennett |
| 6,241,663 | B1 | 6/2001 | Wu et al. | 2003/0163710 A1 | 8/2003 | Ortiz et al. |
| 6,256,523 | B1 | 7/2001 | Diab et al. | 2003/0223621 A1 | 12/2003 | Rowe et al. |
| 6,272,367 | B1 | 8/2001 | Chance | 2004/0003295 A1 | 1/2004 | Elderfield et al. |
| 6,280,381 | B1 | 8/2001 | Malin et al. | 2004/0008875 A1 | 1/2004 | Linares |
| 6,282,303 | B1 | 8/2001 | Brownlee | 2004/0022421 A1 | 2/2004 | Endoh et al. |
| 6,285,895 | B1 | 9/2001 | Ristolainen et al. | 2004/0042642 A1 | 3/2004 | Bolle et al. |
| 6,292,576 | B1 | 9/2001 | Brownlee | 2004/0047493 A1 | 3/2004 | Rowe et al. |
| 6,301,375 | B1 | 10/2001 | Choi | 2004/0114783 A1 | 6/2004 | Spycher et al. |
| 6,301,815 | B1 | 10/2001 | Sliwa | 2004/0120553 A1 | 6/2004 | Stobbe |
| 6,304,767 | B1 | 10/2001 | Soller et al. | 2004/0125994 A1 | 7/2004 | Engels et al. |
| 6,307,633 | B1 | 10/2001 | Mandella et al. | 2004/0179722 A1 | 9/2004 | Moritoki et al. |
| 6,309,884 | B1 | 10/2001 | Cooper et al. | 2004/0240712 A1 | 12/2004 | Rowe et al. |
| 6,317,507 | B1 | 11/2001 | Dolfing et al. | 2004/0240713 A1 | 12/2004 | Hata |
| 6,324,310 | B1 | 11/2001 | Brownlee | 2004/0264742 A1 | 12/2004 | Zhang et al. |
| 6,330,346 | B1 | 12/2001 | Peterson et al. | 2005/0007582 A1 | 1/2005 | Villers et al. |
| 6,404,904 | B1 | 6/2002 | Einighammer et al. | 2005/0125339 A1 | 6/2005 | Tidwell et al. |
| 6,419,361 | B2 | 7/2002 | Cabib et al. | 2005/0169504 A1 | 8/2005 | Black |
| 6,483,929 | B1 | 11/2002 | Murakami et al. | 2005/0180620 A1 | 8/2005 | Takiguchi |
| 6,504,614 | B1 | 1/2003 | Messerschmidt et al. | 2005/0185847 A1 | 8/2005 | Rowe |
| 6,537,225 | B1 | 3/2003 | Mills | 2005/0205667 A1 | 9/2005 | Rowe |
| 6,560,352 | B2 | 5/2003 | Rowe et al. | 2005/0265585 A1 | 12/2005 | Rowe |

| | | | |
|---|---|---|---|
| 2005/0265586 A1 | 12/2005 | Rowe et al. |
| 2005/0265607 A1 | 12/2005 | Chang |
| 2005/0271258 A1 | 12/2005 | Rowe |
| 2006/0002597 A1 | 1/2006 | Rowe |
| 2006/0002598 A1 | 1/2006 | Rowe et al. |
| 2006/0045330 A1 | 3/2006 | Marion |
| 2006/0062438 A1 | 3/2006 | Rowe |
| 2006/0110015 A1 | 5/2006 | Rowe |
| 2006/0115128 A1 | 6/2006 | Mainguet |
| 2006/0171571 A1 | 8/2006 | Chan et al. |
| 2006/0173256 A1 | 8/2006 | Ridder et al. |
| 2006/0202028 A1 | 9/2006 | Rowe |
| 2006/0210120 A1 | 9/2006 | Rowe |
| 2006/0244947 A1 | 11/2006 | Rowe |
| 2006/0274921 A1 | 12/2006 | Rowe |
| 2007/0014437 A1 | 1/2007 | Sato |
| 2007/0030475 A1 | 2/2007 | Rowe et al. |
| 2007/0052827 A1 | 3/2007 | Hiltunen |
| 2007/0116331 A1 | 5/2007 | Rowe et al. |
| 2007/0153258 A1 | 7/2007 | Hernandez |
| 2007/0165903 A1 | 7/2007 | Munro et al. |
| 2008/0008359 A1 | 1/2008 | Beenau et al. |
| 2008/0013806 A1 | 1/2008 | Hamid |
| 2008/0025579 A1 | 1/2008 | Sidlauskas et al. |
| 2008/0025580 A1 | 1/2008 | Sidlauskas et al. |
| 2008/0192988 A1 | 8/2008 | Uludag et al. |
| 2008/0232653 A1 | 9/2008 | Rowe |
| 2008/0260211 A1 | 10/2008 | Bennett et al. |
| 2008/0298649 A1 | 12/2008 | Ennis et al. |
| 2009/0046903 A1 | 2/2009 | Corcoran et al. |
| 2009/0080709 A1 | 3/2009 | Rowe et al. |
| 2009/0092290 A1 | 4/2009 | Rowe |
| 2009/0148005 A1 | 6/2009 | Rowe |
| 2009/0245591 A1 | 10/2009 | Rowe et al. |
| 2010/0067748 A1 | 3/2010 | Rowe |
| 2010/0246902 A1 | 9/2010 | Rowe et al. |
| 2011/0085708 A1 | 4/2011 | Martin et al. |
| 2011/0211055 A1 | 9/2011 | Martin et al. |
| 2011/0235872 A1 | 9/2011 | Rowe et al. |

FOREIGN PATENT DOCUMENTS

| | | |
|---|---|---|
| CN | 1402183 A | 3/2003 |
| CN | 1509454 A | 6/2004 |
| DE | 10153808 | 5/2003 |
| EP | 0 280 418 A1 | 8/1988 |
| EP | 0 372 748 | 6/1990 |
| EP | 0 426 358 B1 | 5/1991 |
| EP | 0 449 335 A2 | 10/1991 |
| EP | 0 573 137 A2 | 12/1993 |
| EP | 0 631 137 A2 | 12/1994 |
| EP | 0 670 143 A1 | 9/1995 |
| EP | 0 681 166 A1 | 11/1995 |
| EP | 0 757 243 A1 | 2/1997 |
| EP | 0 788 000 A2 | 8/1997 |
| EP | 0 801 297 A1 | 10/1997 |
| EP | 0 836 083 A1 | 4/1998 |
| EP | 0 843 986 A2 | 5/1998 |
| EP | 0 869 348 A2 | 10/1998 |
| EP | 0 897 164 A2 | 2/1999 |
| EP | 0 897 691 A2 | 2/1999 |
| EP | 0 317 121 B1 | 5/1999 |
| EP | 0 924 656 A2 | 6/1999 |
| EP | 0 982 583 A1 | 3/2000 |
| EP | 0 990 945 A1 | 4/2000 |
| EP | 1 353 292 | 10/2003 |
| EP | 1 434 162 A2 | 6/2004 |
| FR | 2761180 A1 | 9/1998 |
| JP | 61182174 A | 8/1986 |
| JP | 03-016160 | 1/1991 |
| JP | 7075629 A | 3/1995 |
| JP | 10-127585 | 5/1998 |
| JP | 2001033381 A | 2/2001 |
| JP | 2001-112742 | 4/2001 |
| JP | 2001-184490 A | 7/2001 |
| JP | 2002-133402 A | 5/2002 |
| JP | 2002-517835 A | 6/2002 |
| JP | 2003050993 A | 2/2003 |
| JP | 2003-511101 A | 3/2003 |
| JP | 2003-308520 A | 10/2003 |
| WO | WO 92/00513 A1 | 1/1992 |
| WO | WO 92/17765 A1 | 10/1992 |
| WO | WO 93/00855 A1 | 1/1993 |
| WO | WO 93/07801 A1 | 4/1993 |
| WO | WO 99/27848 A1 | 6/1999 |
| WO | WO 00/30530 | 6/2000 |
| WO | WO 00/46739 A1 | 8/2000 |
| WO | WO 01/15596 A1 | 3/2001 |
| WO | WO 01/18332 A1 | 3/2001 |
| WO | WO 01/20538 | 3/2001 |
| WO | WO 01/27882 A2 | 4/2001 |
| WO | WO 01/52180 A1 | 7/2001 |
| WO | WO 01/52726 A1 | 7/2001 |
| WO | WO 01/53805 A1 | 7/2001 |
| WO | WO 01/65471 A | 9/2001 |
| WO | WO 01/69520 A2 | 9/2001 |
| WO | WO 02/054337 A1 | 7/2002 |
| WO | WO 02/084605 A2 | 10/2002 |
| WO | WO 02/099393 A2 | 12/2002 |
| WO | WO 03/010510 A2 | 2/2003 |
| WO | WO 03/096272 A1 | 11/2003 |
| WO | WO 2004/068388 A2 | 8/2004 |
| WO | WO 2004/068394 | 8/2004 |
| WO | WO 2004/068394 A1 | 8/2004 |
| WO | WO 2004/090786 | 10/2004 |
| WO | WO 2006/049394 A | 5/2006 |
| WO | WO 2006/077446 A2 | 7/2006 |
| WO | WO 2006/093508 A2 | 9/2006 |

OTHER PUBLICATIONS

Ashboum, Julian, Biometrics; Advanced Identity Verification, Springer, 2000, pp. 63-64.
Bantle, John P. et al., "Glucose Measurement in Patients With Diabetes Mellitus With Dermal Interstitial Fluid," Mosby-Year Book, Inc., 9 pages, 1997.
Berkoben, Michael S. et al., "Vascular Access for Hemodialysis," Clinical Dialysis, Third Edition, pp. 2 cover pages and 26-45, 1995.
Blank, T.B. et al., "Transfer of Near-Infrared Multivariate Calibrations Without Standards," Anal. Chem., vol. 68 (1996) p. 2987.
Bleyer, Anthony J. et al., "The Costs of Hospitalizations Due to Hemodialysis Access Management," Nephrology News & Issues, pp. 19, 20 and 22, Jan. 1995.
Brasunas John C. et al., "Uniform Time-Sampling Fourier Transform Spectroscopy," Applied Optics, vol. 36, No. 10, Apr. 1, 1997, pp. 2206-22 10.
Brault, James W., "New Approach to High-Precision Fourier Transform Spectrometer Design," Applied Optics, Vo. 35, No. 16, Jun. 1, 1996, pp. 2891-2896.
Brochure entitled "Improve the Clinical Outcome of Every Patient", In Line Diagnostics, published on or before Oct. 30, 1997, 2 pages.
Cassarly, W.J. et al., "Distributed Lighting Systems: Uniform Light Delivery," Source Unknown, pp. 1698-1702, 1996.
Chang, Chong-Min et al., "An Uniform Rectangular Illuminating Optical System for Liquid Crystal Light Valve Projectors," Euro Display '96 (1996) pp. 257-260.
Coyne, Lawrence J. et al., "Distributive Fiber Optic couplers Using Rectangular Lightguides as Mixing Elements," (Information Gatekeepers, Inc. Brookline, MA, 1979) pp. 160-164.
Daugirdas, JT et al., "Comparison of Methods to Predict the Equilibrated Kt/V (eKt/V) in the Hemo Study," National Institutes of Health, pp. 1-28, Aug. 20, 1996.
de Noord, Onno E., "Multivariate Calibration Standardization," Chemometrics and intelligent Laboratory Systems 25, (1994) pp. 85-97.
Demos, S. G. et al., "Optical Fingerprinting Using Polarisation Contrast Improvement," Electronics Letters, vol. 33, No. 7, pp. 582-584, Mar. 27, 1997.
Depner, Thomas A. et al., "Clinical Measurement of Blood Flow in Hemodialysis Access Fistulae and Grafts by Ultrasound Dilution," Division of Nephrology, University of California, pp. M745-M748, published on or before Oct. 30, 1997.
Despain, Alvin M. et al., "A Large-Aperture Field-Widened Interferometer-Spectrometer for Airglow Studies," Aspen International Conference on Fourier Spectroscopy, 1970, pp. 293-300.

Faber, Nicolaas, "Multivariate Sensitivity for the Interpretation of the Effect of Spectral Pretreatment Methods on Near-Infrared Calibration Model Predictions," Analytical Chemistry, vol. 71, No. 3, Feb. 1, 1999, pp. 557-565.

Fresenius USA, "Determination of Delivered Therapy Through Measurement of Effective Clearance," 2 pages, Dec. 1994.

Geladi, Paul et al., A Multivariate NIR Study of Skin Alterations in Diabetic Patients as Compared to Control Subjects,J. Near Infrared Spectrosc., vol. 8 (2000) pp. 217-227.

Hakim, Raymond M. et al., "Effects of Dose of Dialysis on Morbidity and Mortality," American Journal of Kidney Diseases, vol. 23, No. 5, pp. 661-669, May 1994.

Jacobs, Paul et al., "A Disposable Urea Sensor for Continuous Monitoring of Hemodialysis Efficiency," ASAIO Journal, pp. M353-M358, 1993.

Keshaviah, Prakash R. et al., "On-Line Monitoring of the Delivery of the Hemodialysis Prescription," Pediatric Nephrology, vol. 9, pp. S2-S8, 1995.

Krivitski, Nikolai M., "Theory and Validation of Access Flow Measurement by Dilution Technique During Hemodialysis," Kidney International, vol. 48, pp. 244-250, 1995.

Lee et al., "Fingerprint Recognition Using Principal Gabor Basis Function", Proceedings of 2001 International Symposium on Intelligent Multimedia, Video and Speech Processing, May 2-4, 2001, Sections 2-3.

Maltoni et al., "Handbook of Fingerprint Recognition," 2005, pp. 58-61.

Marbach, Ralf, "Measurement Techniques for IR Spectroscopic Blood Glucose Determination," Fortschritt Bericht, Series 8: Measurement and Control Technology, No. 346, pp. cover and 1-158, Mar. 28, 1994.

Mardia, K.V. et al., "Chapter 11—Discriminant Analysis," Multivariate Analysis, pp. 2 cover pages and 300-325, 1979.

Nichols, Michael G. et al., "Design and Testing of a White-Light, Steady-State Diffuse Reflectance Spectrometer for Determination of Optical Properties of Highly Scattering Systems," Applied Optics, vol. 36, No. 1, pp. 93-104, Jan. 1, 1997.

Nixon, Kristin A. et al., "Novel Spectroscopy-Based Technology for Biometric and Liveness Verification", Technology for Human Identification. Proceedings od SPIE, vol. 5404, No. 1, XP-002458441, Apr. 12-13, 2004, pp. 287-295 (ISSN: 0277-786x).

Pan et al., "Face Recognition in Hyperspectral Images", IEEE Transactions on Pattern Analysis and Machine Intelligence vol. 25, No. 12, Dec. 2003.

Ripley, B. D., "Chapter 3—Linear Discriminant Analysis," Pattern Recognition and Neural Networks, pp. 3 cover pages and 91-120, 1996.

Ronco, C. et al., "On-Line Urea Monitoring : A Further Step Towards Adequate Dialysis Prescription and Delivery," The International Journal of Artificial Organs, vol. 18, No. 9, pp. 534-543, 1995.

Ross et al., "A Hybrid Fingerprint Matcher," Pattern Recognition 36, The Journal of the Pattern Recognition Society, 2003 Elsevier Science Ltd., pp. 1661-1673.

Selvaraj et al., Fingerprint Verification Using Wavelet Transform, Proceedings of the Fifth International Conference on Computational Intelligence and Multimedia Applications, IEEE, 2003.

Service, F. John et al., "Dermal Interstitial Glucose as an Indicator of Ambient Glycemia," Diabetes Care, vol. 20, No. 9, 8 pages, Aug. 1997.

Sherman, Richard A., "Chapter 4—Recirculation in the Hemodialysis Access," Principles and Practice of Dialysis, pp. 2 cover pages and 38-46, 1994.

Sherman, Richard A., "The Measurement of Dialysis Access Recirculation," American Journal of Kidney Diseases, vol. 22, No. 4, pp. 616-621, Oct. 1993.

Steuer, Robert R. et al., "A New Optical Technique for Monitoring Hematocrit and Circulating Blood Volume: Its Application in Renal Dialysis," Dialysis & Transplantation, vol. 22, No. 5, pp. 260-265, May 1993.

Webb, Paul, "Temperatures of Skin, Subcutaneous Tissue, Muscle and Core in Resting Men In Cold, Comfortable and Hot Conditions," European Journal of Applied Physiology, vol. 64, pp. 471-476, 1992.

Zavala, Albert et al., "Using Fingerprint Measures to Predict Other Anthropometric Variables," Human Factors, vol. 17, No. 6, pp. 591-602, 1975.

Rowe, "LumiGuard: A Novel Spectroscopic Sensor for Biometric Security Applications", American Chemical Society 225th National Meeting, Mar. 25, 2003, 20 pages.

Chinese Patent Application No. 2006/80038579.4, First Office Action mailed on Mar. 23, 2011, 7 pages.

European Patent Application No. 10166537.0, Extended European Search Report mailed on Jun. 1, 2011, 7 pages.

International Search Report and Written Opinion of PCT/US2008/066585 mailed on Oct. 30, 2008, 10 pages.

International Search Report and Written Opinion of PCT/US2010/025463 mailed on Jun. 30, 2010, 12 pages.

International Search Report of PCT/US2010/046852 mailed on Dec. 29, 2010, 5 pages.

Rowe, et al. "Multispectral Fingerprint Image Acquisition," Advances in Biometrics, 2008, 22 pages.

\* cited by examiner

WHITE-LIGHT SPECTRAL BIOMETRIC SENSORS

CROSS-REFERENCES TO RELATED APPLICATIONS

This application is a continuation of copending U.S. patent application Ser. No. 11/458,607, entitled "WHITE-LIGHT SPECTRAL BIOMETRIC SENSORS," filed Jul. 19, 2006, by Robert K. Row et al. ("the 607 application") The entire disclosure of which is incorporated herein by reference for all purposes.

The '607 application is a continuation-in-part of copending U.S. patent application Ser. No. 10/818,698, entitled "MULTISPECTRAL BIOMETRIC SENSOR," filed Apr. 5, 2004 by Robert K. Rowe et al. ("the '698 application"). The '698 application is a nonprovisional of each of the following provisional applications: U.S. Prov. Pat. Appl. No. 60/460,247, entitled "NONINVASIVE ALCOHOL MONITOR," filed Apr. 4, 2003; U.S. Prov. Pat. Appl. No. 60/483,281, entitled "HYPERSPECTRAL FINGERPRINT READER," filed Jun. 27, 2003 by Robert K. Rowe et al.; U.S. Prov. Pat. Appl. No. 60/504,594, entitled "HYPERSPECTRAL FINGERPRINTING," filed Sep. 18, 2003; and U.S. Prov. Pat. Appl. No. 60/552,662, entitled "OPTICAL SKIN SENSOR FOR BIOMETRICS," filed Mar. 10, 2004. The entire disclosure of each of the foregoing applications is incorporated herein by reference for all purposes.

The '607 application is also a continuation-in-part of copending U.S. patent application Ser. No. 11/219,006, entitled "COMPARATIVE TEXTURE ANALYSIS OF TISSUE FOR BIOMETRIC SPOOF DETECTION," filed Sep. 1, 2005 by Robert K. Rowe ("the '006 application"). The '006 application is a continuation-in-part of U.S. patent application Ser. No. 10/818,698, entitled "MULTISPECTRAL BIOMETRIC SENSOR," filed Apr. 5, 2004 by Robert K. Row. et al., which is a nonprovisional of each of U.S. Prov. Pat. Appl. No. 60/460,247, filed Apr. 4, 2003, U.S. Prov. Pat. Appl. No. 60/483,281, filed Jun. 27, 2003, U.S. Prov. Pat. Appl. No. 60/504,594, filed Sep. 18, 2003, and U.S. Prov. Pat. Appl. No. 60/552,662, filed Mar. 10, 2004. The entire disclosure of each of the foregoing applications is incorporated herein by reference for all purposes.

The '006 application is also a continuation-in-part of U.S. patent application Ser. No. 11/115,100, entitled "MULTISPECTRAL IMAGING BIOMETRICS," filed Apr. 25, 2005 by Robert K. Rowe, which is a nonprovisional of each of U.S. Prov. Pat. Appl. No. 60/576,364, filed Jun. 1, 2004, U.S. Prov. Pat. Appl. No. 60/600,867, filed Aug. 11, 2004, U.S. Prov. Pat. Appl. No. 60/610,802, filed Sep. 17, 2004, U.S. Prov. Pat. Appl. No. 60/654,354, filed Feb. 18, 2005, and U.S. Prov. Pat. Appl. No. 60/659,024, filed Mar. 4, 2005. The entire disclosure of each of the foregoing applications is incorporated herein by reference for all purposes.

The '006 application is also a continuation-in-part of U.S. patent application Ser. No. 11/115,101, entitled "MULTISPECTRAL BIOMETRIC IMAGING," filed Apr. 25, 2005 by Robert K. Rowe and Stephen P. Corcoran, which is a nonprovisional of each of U.S. Prov. Pat. Appl. No. 60/576,364, filed Jun. 1, 2004, U.S. Prov. Pat. Appl. No. 60/600,867, filed Aug. 11, 2004, U.S. Prov. Pat. Appl. No. 60/610,802, filed Sep. 17, 2004, U.S. Prov. Pat. Appl. No. 60/654,354, filed Feb. 18, 2005, and U.S. Prov. Pat. Appl. No. 60/659,024, filed Mar. 4, 2005. The entire disclosure of each of the foregoing references is incorporated herein by reference for all purposes.

The '006 application is also a continuation-in-part of U.S. patent application Ser. No. 11/115,075, entitled "MULTISPECTRAL LIVENESS DETERMINATION," FILED Apr. 25, 2005 by Robert K. Rowe, which is a nonprovisional of each of U.S. Prov. Pat. Appl. No. 60/576,364, filed Jun. 1, 2004, U.S. Prov. Pat. Appl. No. 60/600,867, filed Aug. 11, 2004, U.S. Prov. Pat. Appl. No. 60/610,802, filed Sep. 17, 2004, U.S. Prov. Pat. Appl. No. 60/654,354, filed Feb. 18, 2005, and U.S. Prov. Pat. Appl. No. 60/659,024, filed Mar. 4, 2005. The entire disclosure of each of the foregoing references is incorporated herein by reference for all purposes.

This application is also related to each of the following applications, the entire disclosure of each of which is incorporated herein by reference for all purposes: concurrently filed U.S. patent application Ser. No. 11/458,619, entitled "TEXTURE-BIOMETRICS SENSOR," filed by Robert K. Rowe; and U.S. patent application Ser. No. 09/874,740, entitled "APPARATUS AND METHOD OF BIOMETRIC DETERMINATION USING SPECIALIZED OPTICAL SPECTROSCOPY SYSTEM," filed Jun. 5, 2001.

BACKGROUND OF THE INVENTION

This application relates generally to biometrics. More specifically, this application relates to methods and systems for performing biometric measurements that use spectral information.

"Biometrics" refers generally to the statistical analysis of characteristics of living bodies. One category of biometrics includes "biometric identification," which commonly operates under one of two modes to provide automatic identification of people or to verify purported identities of people. Biometric sensing technologies measure the physical features or behavioral characteristics of a person and compare those features to similar prerecorded measurements to determine whether there is a match. Physical features that are commonly used for biometric identification include faces, irises, hand geometry, vein structure, and fingerprint patterns, which is the most prevalent of all biometric-identification features. Current methods for analyzing collected fingerprints include optical, capacitive, radio-frequency, thermal, ultrasonic, and several other less common techniques.

Most of the fingerprint-collection methods rely on measuring characteristics of the skin at or very near the surface of a finger. In particular, optical fingerprint readers typically rely on the presence or absence of a difference in the index of refraction between the sensor platen and the finger placed on it. When an air-filled valley of the fingerprint is above a particular location of the platen, total internal reflectance ("TIR") occurs in the platen because of the air-platen index difference. Alternatively, if skin of the proper index of refraction is in optical contact with the platen, then the TIR at this location is "frustrated," allowing light to traverse the platen-skin interface. A map of the differences in TIR across the region where the finger is touching the platen forms the basis for a conventional optical fingerprint reading. There are a number of optical arrangements used to detect this variation of the optical interface in both bright-field and dark-field optical arrangements. Commonly, a single, quasimonochromatic beam of light is used to perform this TIR-based measurement.

There also exists non-TIR optical fingerprint sensors. In most cases, these sensors rely on some arrangement of quasi-monochromatic light to illuminate the front, sides, or back of a fingertip, causing the light to diffuse through the skin. The fingerprint image is formed due to the differences in light transmission across the skin-platen boundary for the ridge and valleys. The difference in optical transmission are due to changes in the Fresnel reflection characteristics due to the presence or absence of any intermediate air gap in the valleys, as known to one of familiarity in the art.

Optical fingerprint readers are particularly susceptible to image quality problems due to non-ideal conditions. If the skin is overly dry, the index match with the platen will be compromised, resulting in poor image contrast. Similarly, if the finger is very wet, the valleys may fill with water, causing an optical coupling to occur all across the fingerprint region and greatly reducing image contrast. Similar effects may occur if the pressure of the finger on the platen is too little or too great, the skin or sensor is dirty, the skin is aged and/or worn, or overly fine features are present such as may be the case for certain ethnic groups and in very young children. These effects decrease image quality and thereby decrease the overall performance of the fingerprint sensor. In some cases, commercial optical fingerprint readers incorporate a thin membrane of soft material such as silicone to help mitigate these effects and restore performance. As a soft material, the membrane is subject to damage, wear, and contamination, limiting the use of the sensor without maintenance.

Optical fingerprint readers, such as those based on TIR, as well as other modalities such as capacitance, RF, and others, typically produce images that are affected to some degree by the nonideal imaging conditions present during acquisition. An analysis of the textural characteristics of the resulting images is thus affected by the sampling conditions, which may limit or obscure the ability to observe the textural characteristics of the person's skin. The consequence of this is that texture is of limited utility in such sensing modalities.

Biometric sensors, particularly fingerprint biometric sensors, are generally prone to being defeated by various forms of spoof samples. In the case of fingerprint readers, a variety of methods are known in the art for presenting readers with a fingerprint pattern of an authorized user that is embedded in some kind of inanimate material such as paper, gelatin, epoxy, latex, and the like. Thus, even if a fingerprint reader can be considered to reliably determine the presence or absence of a matching fingerprint pattern, it is also critical to the overall system security to ensure that the matching pattern is being acquired from a genuine, living finger, which may be difficult to ascertain with many common sensors.

Another way in which some biometric systems may be defeated is through the use of a replay attack. In this scenario, an intruder records the signals coming from the sensor when an authorized user is using the system. At a later time, the intruder manipulates the sensor system such that the prerecorded authorized signals may be injected into the system, thereby bypassing the sensor itself and gaining access to the system secured by the biometric.

A common approach to making biometric sensors more robust, more secure, and less error-prone is to combine sources of biometric signals using an approach sometimes referred to in the art as using "dual," "combinatoric," "layered," "fused," "multibiometric," or "multifactor biometric" sensing. To provide enhanced security in this way, biometric technologies are combined in such a way that different technologies measure portions of the body at the same time and are resistant to being defeated by using different samples or techniques to defeat the different sensors that are combined. When technologies are combined in a way that they view the same part of the body they are referred to as being "tightly coupled."

The accuracy of noninvasive optical measurements of physiological analytes such as glucose, alcohol, hemoglobin, urea, and cholesterol can be adversely affected by variation of the skin tissue. In some cases it is advantageous to measure one or more physiological analytes in conjunction with a biometric measurement. Such dual measurement has potential interest and application to both commercial and law-enforcement markets.

There is accordingly a general need in the art for improved methods and systems for biometric sensing and analyte estimation using multispectral imaging systems and methods.

BRIEF SUMMARY OF THE INVENTION

Embodiments of the invention provide methods and systems for performing biometric functions. White light is used to illuminate a purported skin site and a color imager is used to collect light scattered from the purported skin site for the generation of multispectral data. These multispectral data may be generated in the form of multiple images of the skin site collected with different illumination wavelengths, which correspond to different volumes of illuminated tissue. These data are then subjected to different types of analyses depending on specific aspects of the biometric function to be performed.

Thus, in a first set of embodiments, a biometric sensor is provided. A white-light illumination subsystem is disposed to illuminate a purported skin site of an individual with white light. A detection subsystem is disposed to receive light scattered from the purported skin site and comprises a color imager on which the received light is incident. A computational unit is interfaced with the detection subsystem. The computational unit has instructions for deriving a plurality of spatially distributed images of the purported skin site from the received light with the color imager. The plurality of spatially distributed images correspond to different volumes of illuminated tissue of the individual. The computational unit also has instructions for analyzing the plurality of spatially distributed images to perform a biometric function.

In one of these embodiments, the biometric function comprises an antispoofing function and the instructions for analyzing the plurality of spatially distributed images comprise instructions for determining whether the purported skin site comprises living tissue. In another of these embodiments, the instructions for analyzing the plurality of spatially distributed images to perform the biometric function comprise instructions for analyzing the plurality of spatially distributed images to estimate a demographic or anthropometric characteristic of the individual. In still another of these embodiments, the instructions for analyzing the plurality of spatially distributed images to perform the biometric function comprise instructions for analyzing the plurality of spatially distributed images to determine a concentration of an analyte in blood of the individual.

In some embodiments, the biometric sensor may further comprise a platen in contact with the purported skin site, with the white-light illumination subsystem being adapted to illuminate the purported skin site through the platen. In other embodiments, the white-light illumination subsystem may instead be adapted to illuminate the purported skin site when the skin site is not in physical contact with the biometric sensor.

The white light may be provided in different ways in different embodiments. For example, in one embodiment, the white-light illumination subsystem comprises a broadband source of white light. In another embodiment, the white-light illumination subsystem comprises a plurality of narrow-band light sources and an optical arrangement to combine light provided by the plurality of narrow-band light sources. The plurality of narrow-band light sources may provide light at wavelengths that correspond to each of a set of primary colors. In some cases, the purported skin site and an illumination region where the purported skin site is illuminated are in relative motion.

Some embodiments make use of polarization by including a first polarizing in the illumination system disposed to polarize the white light. The detection system then comprises a second polarizer disposed to encounter the received light. The first and second polarizers may be crossed relative to each other. In other embodiments, the first and second polarizers may be parallel. In some embodiments, the first polarizer may be omitted while retaining the second. In some embodiments, two or more of these polarization options may be combined in a single device. The detection system may also sometimes include an infrared filter disposed to encounter the received light before the received light is incident on the color imager.

In certain instances, the purported skin site is a volar surface of a finger or hand and the biometric function comprises a biometric identification. The instructions for analyzing the plurality of spatially distributed images comprise instructions for deriving a surface fingerprint or palmprint image of the purported skin site from the plurality of spatially distributed images. The surface fingerprint or palmprint image is then compared with a database of fingerprint or palmprint images to identify the individual. In other embodiment where the biometric function comprises a biometric identification, the instructions for analyzing the plurality of spatially distributed images instead comprise instructions for comparing the plurality of spatially distributed images with a database of multispectral images to identify the individual.

In a second set of embodiments, a method is provided of performing a biometric function. A purported skin site of an individual is illuminated with white light. Light scattered from the purported skin site is received with a color imager on which the received light is incident. A plurality of spatially distributed images of the purported skin site are derived, with the plurality of spatially distributed images corresponding to different volumes of illuminated tissue of the individual. The plurality of spatially distributed images are analyzed to perform the biometric function.

In some of these embodiments, the biometric function comprises an antispoofing function and analyzing the plurality of spatially distributed images comprises determining whether the purported skin site comprises living tissue. In other of these embodiments, the plurality of spatially distributed images are analyzed to estimate a demographic or anthropometric characteristic of the individual. In still different ones of these embodiments, the plurality of spatially distributed images are analyzed to determine a concentration of an analyte in blood of the individual.

The purported skin site may sometimes be illuminated by directing the white light through a platen in contact with the purported skin site. In some instances, the purported skin site may be illuminated with a broadband source of white light, while in other instances a plurality of narrow-band beams, perhaps corresponding to a set of primary colors, may be generated and combined. The purported skin site might sometimes be in relative motion with an illumination region where the purported skin site is illuminated.

In one embodiment the while light is polarized with a first polarization and the received light scattered from the purported skin site is polarized with a second polarization. The first and second polarizations may be substantially crossed relative to each other or may be substantially parallel to each other. The received light may sometimes be filtered at infrared wavelengths before the received light is incident on the color imager.

In some instances, the biometric function comprises a biometric identification. For instance, the purported skin site could be a volar surface of a finger or hand. Analysis of the plurality of spatially distributed images could then proceed by deriving a surface fingerprint or palmprint image of the purported skin site from the plurality of spatially distributed images and comparing the surface fingerprint or palmprint image with a database of fingerprint or palmprint images. In an alternative embodiment, the plurality of spatially distributed images could be compared with a database of multispectral images to identify the individual.

BRIEF DESCRIPTION OF THE DRAWINGS

A further understanding of the nature and advantages of the present invention may be realized by reference to the remaining portions of the specification and the drawings wherein like reference labels are used throughout the several drawings to refer to similar components. In some instances, reference labels include a numerical portion followed by a latin-letter suffix; reference to only the numerical portion of reference labels is intended to refer collectively to all reference labels that have that numerical portion but different latin-letter suffices.

DETAILED DESCRIPTION OF THE INVENTION

1. Overview

Figure 1:
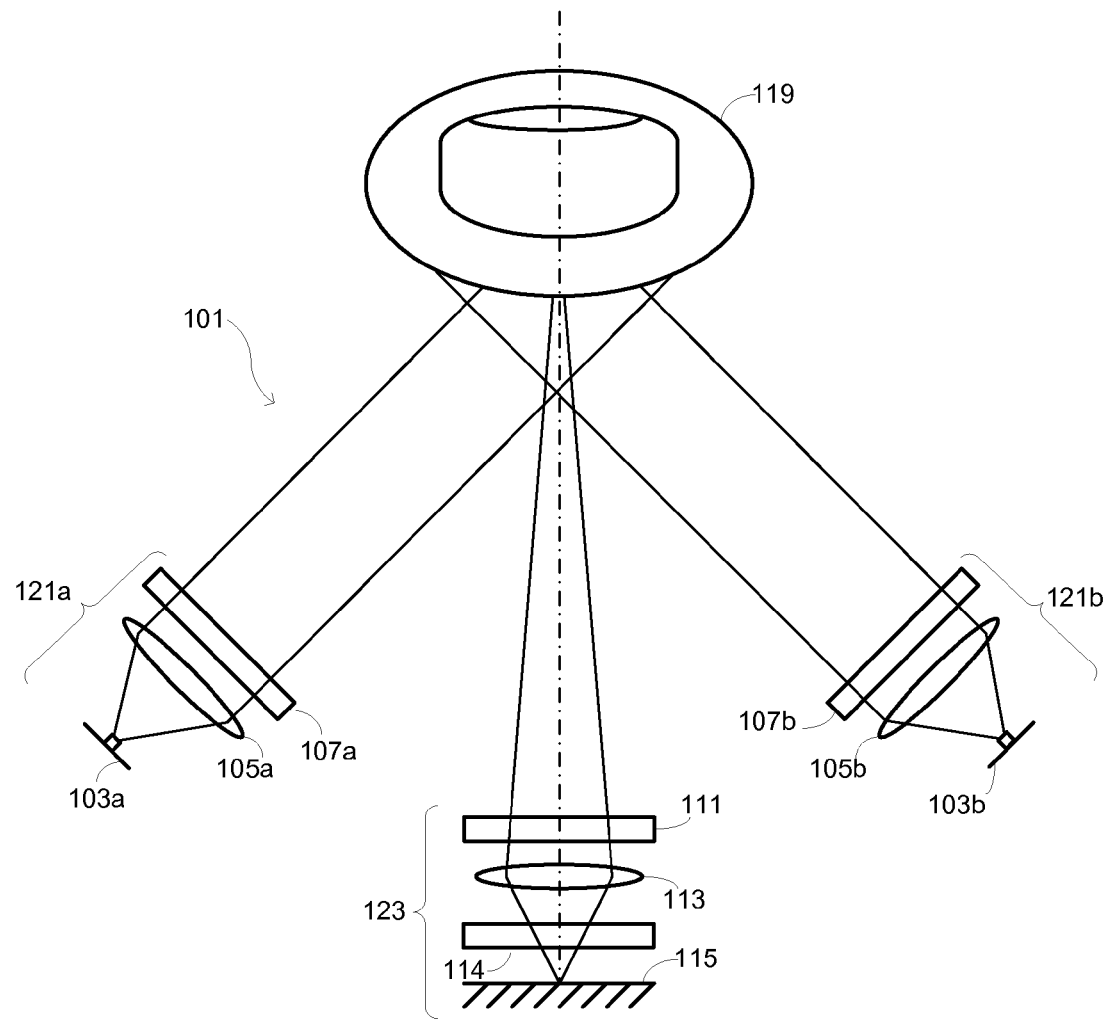
FIG. 1 provides a front view of a noncontact biometric sensor in one embodiment of the invention.

Embodiments of the invention provide methods and systems that allow for the collection and processing of a variety of different types of biometric measurements, including integrated, multifactor biometric measurements in some embodiments. These measurements may provide strong assurance of a person's identity, as well as of the authenticity of the biometric sample being taken. In some embodiments, a sensor uses white light that penetrates the surface of the person's skin, and scatters within the skin and/or the underlying tissue. As used herein, "white light" refers to light that has a spectral composition amenable to separation into constituent wavelength bands, which in some cases may comprise primary colors. The usual primary colors used to define white light are red, green, and blue, but other combinations may be used in other instances, as will be known to those of skill in the art. For clarity, it is emphasized that "white light" as used herein might not appear white to a human observer and might have a distinct tint or color associated with it because of the exact wavelength distribution and intensity of the constituent wavelength bands. In other cases, the white light may comprise one or more bands in the ultraviolet or infrared spectral regions. In some cases, the white light might not even be visible at all to a human observer when it consists of wavelength bands in the infrared and/or ultraviolet spectral regions. A portion of the light scattered by the skin and/or underlying tissue exits the skin and is used to form an image of the structure of the tissue at and below the surface of the skin. Because of the wavelength-dependent properties of the skin, the image formed from each wavelength of light comprised by the white light may be different from images formed at other wavelengths. Accordingly, embodiments of the invention collect images in such a way that characteristic spectral and spatial information may be extracted from the resulting image.

In some applications, it may be desirable to estimate other parameters and characteristics of a body, either independently or in combination with a biometric measurement. For example, in one specific such embodiment, an ability is provided to measure analyte levels of a person simultaneously with measurement of a fingerprint pattern. Applications to law enforcement may be found in embodiments where the measure analyte comprises a blood-alcohol level of the person; such embodiments also enable a variety of commercial applications that include restricting motor-vehicle access. In this way, the analyte measurement and the identity of the person on whom the measurement is made may be inextricably linked.

Skin composition and structure is very distinct, very complex, and varies from person to person. By performing optical measurements of the spatiospectral properties of skin and underlying tissue, a number of assessments may be made. For example, a biometric-identification function may be performed to identify or verify whose skin is being measured, a liveness function may be performed to assure that the sample being measured is live and viable skin and not another type of material, estimates may be made of a variety of physiological parameters such as age gender, ethnicity, and other demographic and anthropometric characteristics, and/or measurements may be made of the concentrations of various analytes and parameters including alcohol, glucose, degrees of blood perfusion and oxygenation, biliruben, cholesterol, urea, and the like.

The complex structure of skin may be used in different embodiments to tailor aspects of the methods and systems for particular functions. The outermost layer of skin, the epidermis, is supported by the underlying dermis and hypodermis. The epidermis itself may have five identified sublayers that include the stratum corneum, the stratum lucidum, the stratum granulosum, the stratum spinosum, and the stratum germinativum. Thus, for example, the skin below the top-most stratum corneum has some characteristics that relate to the surface topography, as well as some characteristics that change with depth into the skin. While the blood supply to skin exists in the dermal layer, the dermis has protrusions into the epidermis known as "dermal papillae," which bring the blood supply close to the surface via capillaries. In the volar surfaces of the fingers, this capillary structure follows the pattern of the friction ridges and valleys on the surface. In some other locations on the body, the structure of the capillary bed may be less ordered, but is still characteristic of the particular location and person. As well, the topography of the interface between the different layers of skin is quite complex and characteristic of the skin location and the person. While these sources of subsurface structure of skin and underlying tissue represent a significant noise source for non-imaging optical measurements of skin for biometric determinations or analyte measurements, the structural differences are manifested by spatiospectral features that can be compared favorably through embodiments of the invention.

In some instances, inks, dyes and/or other pigmentation may be present in portions of the skin as topical coating or subsurface tattoos. These forms of artificial pigmentation may or may not be visible to the naked human eye. However, if one or more wavelengths used by the apparatus of the present invention is sensitive to the pigment, the sensor can be used in some embodiments to verify the presence, quantity and/or shape of the pigment in addition to other desired measurement tasks.

In general, embodiments of the present invention provide methods and systems that collect spatiospectral information that may be represented in a multidimensional data structure that has independent spatial and spectral dimensions. In certain instances, the desired information is contained in just a portion of the entire multidimensional data structure. For example, estimation of a uniformly distributed, spectrally active compound may require just the measured spectral characteristics, which may be extracted from the overall multidimensional data structure. In such cases, the overall system design may be simplified to reduce or eliminate the spatial component of the collected data by reducing the number of image pixels, even to a limit of a single pixel. Thus, while the systems and methods disclosed are generally described in the context of spatiospectral imaging, it will be recognized that the invention encompasses similar measurements in which the degree of imaging is greatly reduced, even to the point where there is a single detector element.

2. Noncontact Biometric Sensors

One embodiment of the invention is depicted with the schematic diagram of FIG. 1, which shows a front view of a noncontact biometric sensor 101. The sensor 101 comprises an illumination subsystem 121 having one or more light sources 103 and a detection subsystem 123 with an imager 115. The figure depicts an embodiment in which the illumination subsystem 121 comprises a plurality of illumination subsystems 121*a* and 121*b*, but the invention is not limited by the number of illumination or detection subsystems 121 or 123. For example, the number of illumination subsystems 121 may conveniently be selected to achieve certain levels of illumination, to meet packaging requirements, and to meet other structural constraints of the sensor 101. Illumination light passes from the source 103 through illumination optics 105 that shape the illumination to a desired form, such as in the form of flood light, light lines, light points, and the like. The illumination optics 105 are shown for convenience as consisting of a lens but may more generally include any combination of one or more lenses, one or more mirrors, and/or other optical elements. The illumination optics 105 may also comprise a scanner mechanism (not shown) to scan the illumination light in a specified one-dimensional or two-dimensional pattern. The light source 103 may comprise a point source, a line source, an area source, or may comprise a series of such sources in different embodiments. In one embodiment, the illumination light is provided as polarized light, such as by disposing a linear polarizer 107 through which the light passes before striking a finger 119 or other skin site of the person being studied. Embodiments like those shown in FIG. 1 are referred to herein as "noncontact" sensors because the imaged skin site may be positioned to interact with the light without being in contact with any solid surface. In "contact" biometric sensors described in detail below, the imaged skin site is in contact with some solid surface such as a platen or light detector.

In some instances, the light source 103 comprises a white-light source, which may be provided as a broad-band source or as a collection of narrow-band emitters in different embodiments. Examples of broad-band sources include white-light emitting diodes ("LEDs"), incandescent bulbs or glowbars, and the like. Collections of narrow-band emitters may comprise quasimonochromatic light sources having primary-color wavelengths, such as in an embodiment that includes a red LED or laser diode, a green LED or laser diode, and a blue LED or laser diode.

An alternative mechanism for reducing the directly reflected light makes use of optical polarizers. Both linear and circular polarizers can be employed advantageously to make the optical measurement more sensitive to certain skin depths, as known to on familiar in the art. In the embodiment illustrated in FIG. 1, the illumination light is polarized by linear polarizer 107. The detection subsystem 123 may then also include a linear polarizer 111 that is arranged with its optical axis substantially orthogonal to the illumination polarizer 107. In this way, light from the sample must undergo multiple scattering events to significantly change it state of polarization. Such events occur when the light penetrates the surface of the skin and is scattered back to the detection subsystem 123 after many scatter events.

Conversely, the use of two polarizers 107 and 111 may also be used to increase the influence of directly reflected light by arranging the polarizer 111 to be substantially parallel to polarizer 107. In some systems, it may be advantageous to combine two or more polarization configurations in a single device to enable the collection of multispectral data collected under two different polarization conditions (i.e. under crossed-polarization and under parallel-polarization conditions). In other embodiments, either polarizer 107 or 111, or both, may be omitted, allowing for the collection of substantially randomly polarized light.

The detection subsystem 123 may incorporate detection optics that comprise lenses, mirrors, phase plates and wave-front coding devices, and/or other optical elements that form an image onto the detector 115. The detection optics 113 may also comprise a scanning mechanism (not shown) to relay portions of the overall image onto the detector 115 in sequence. In all cases, the detection subsystem 123 is configured to be sensitive to light that has penetrated the surface of the skin and undergone optical scattering within the skin and/or underlying tissue before exiting the skin.

Figure 2A:
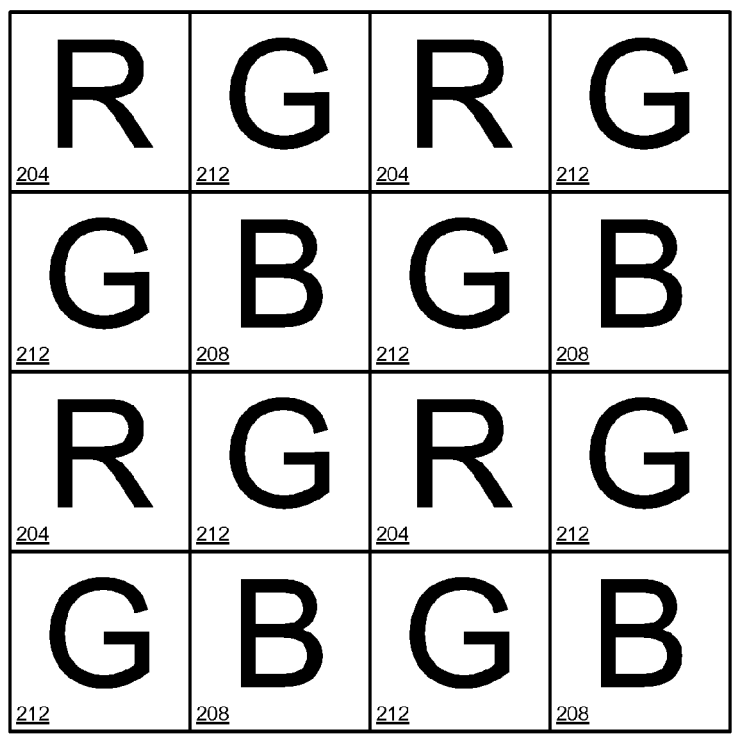
FIG. 2A provides an illustration of a structure for a Bayer color filter array, which may be used in embodiments of the invention.
Figure 2B:
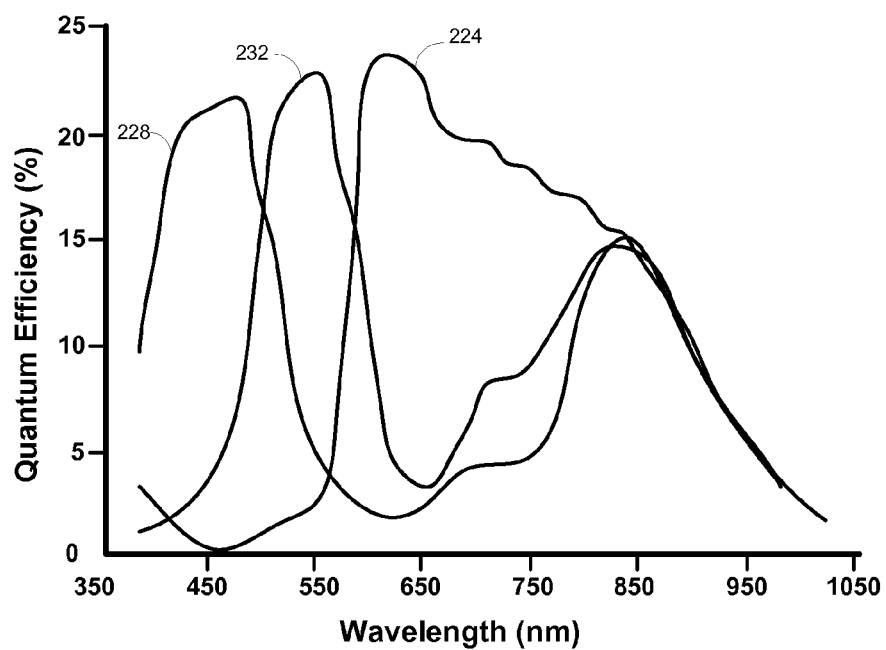
FIG. 2B is a graph showing color response curves for a Bayer color filter array like that illustrated in FIG. 2A.

In embodiments where white light is used, the detector 115 may comprise a Bayer color filter array in which filter elements corresponding to a set of primary colors are arranged in a Bayer pattern. An example of such a pattern is shown in FIG. 2A for an arrangement that uses red 204, green 212, and blue 208 color filter elements. In some instances, the detector subsystem 123 may additionally comprise an infrared filter 114 disposed to reduce the amount of infrared light detected. As seen from the color response curve for a typical Bayer filter array shown in FIG. 2B, there is generally some overlap in the spectral ranges of the red 224, green 232, and blue 228 transmission characteristics of the filter elements. As evident particularly in the curves for the green 232 and blue 228 transmission characteristics, the filter array may allow the transmission of infrared light. This is avoided with the inclusion of an infrared filter 114 as part of the detector subsystem. In other embodiments, the infrared filter 114 may be omitted and one or more light sources 103 that emit infrared light may be incorporated. In this way, all color filter elements 204, 208, and 212 may allow the light to substantially pass through, resulting in an infrared image across the entire detector 115.

Figure 3:
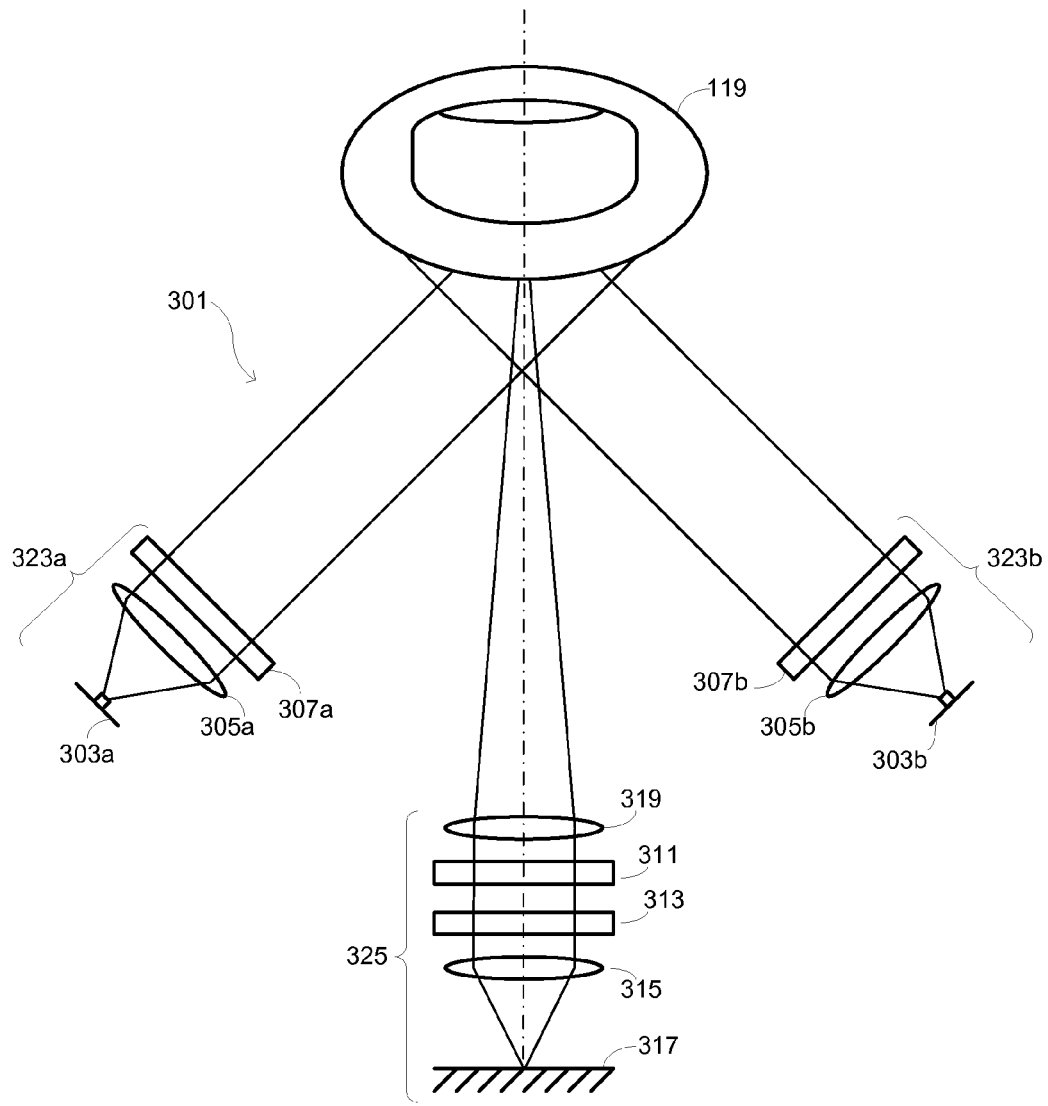
FIG. 3 provides a front view of a noncontact biometric sensor in another embodiment of the invention.

Another embodiment of a noncontact biometric sensor is shown schematically with the front view of FIG. 3. In this embodiment, the biometric sensor 301 comprises an illumination subsystem 323 and a detection subsystem 325. Similar to the embodiment described in connection with FIG. 1, there may be multiple illumination subsystems 323 in some embodiments, with FIG. 3 showing a specific embodiment having two illumination subsystems 323. A white-light source 303 comprised by the illumination subsystem 323 may be any source of white light, including the broad-band or combination of narrow-band sources described above. Light from the white-light source 303 passes through illumination optics 305 and a linear polarizer 307 before passing into the skin site 119. A portion of the light is diffusely reflected from the skin site 119 into the detection subsystem 325, which comprises imaging optics 315 and 319, a linear polarizer 311, and a dispersive optical element 313. The dispersive element 313 may comprise a one- or two-dimensional grating, which may be transmissive or reflective, a prism, or any other optical component known in the art to cause a deviation of the path of light as a function of the light's wavelength. In the illustrated embodiment, the first imaging optics 319 acts to collimate light reflected from the skin site 119 for transmission through the linear polarizer 311 and dispersive element 313. Spectral components of the light are angularly separated by the dispersive element 313 and are separately focused by the second imaging optics 315 onto a detector. As discussed in connection with FIG. 1, when the optical axis of the polarizers 307 and 311 are oriented to be substantially orthogonal to each other, polarizers 307 and 311 respectively comprised by the illumination and detection subsystems 323 and 325 act to reduce the detection of directly reflected light at the detector 317. The polarizers 307, 311 may also be oriented such that their optical axes are substantially parallel, which will increase the detection of directly reflected light at the detector 317. In some embodiments, either polarizer 307 or 311, or both, may be omitted.

The image generated from light received at the detector is thus a "coded" image in the manner of a computer tomographic imaging spectrometer ("CTIS"). Both spectral and spatial information are simultaneously present in the resulting image. The individual spectral patters may be obtained by mathematical inversion or "reconstruction" of the coded image.

Figure 4:
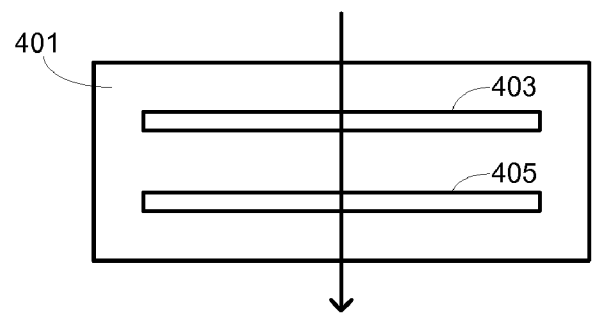
FIG. 4 provides a top view of a sensor configuration that collects data during relative motion between a skin site and an optically active region of the sensor.

The description of the contactless sensor of FIG. 1 noted that a scanner mechanism may be provided to scan the illumination light. This is an example of a more general class of embodiments in which there is relative motion of the illumination region and skin site. In such embodiments, the image may be constructed by building up separate image portions collected during the relative motion. Such relative motion may also be achieved in embodiments that configure the sensor in a swipe configuration, in which the user is instructed to translate the skin site. One example of a swipe sensor is shown in top view with the schematic illustration of FIG. 4. In this figure, the illumination region and detection region 405 of a sensor 401 are substantially collinear. In some embodiments of a swipe sensor 401, there may be more than a single illumination region. For example, there may be a plurality of illumination regions arranged on either side of the detection region 405. In some embodiments, the illumination region 403 may partially or fully overlay the detection region. The image data are collected with the sensor by translating a finger or other body part through the optically active region, as indicated by the arrow in FIG. 4. A swipe sensor may be implemented with any of the contactless sensor configurations described above, although in some implementations it may be used with a contact configuration, examples of which are described in detail below. The light that is received sequentially from discrete portions of the skin site is used to build up the image that is subsequently used for biometric applications.

Figure 5:
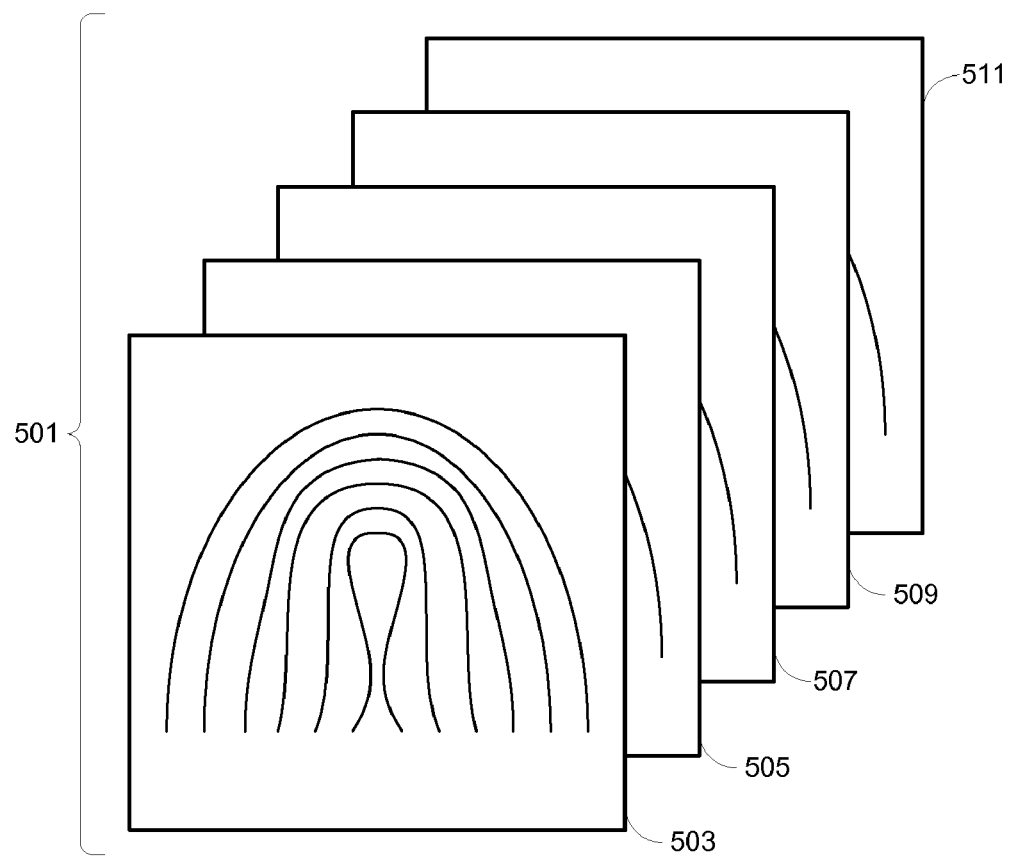
FIG. 5 illustrates a multispectral datacube that may be used in certain embodiments of the invention.

The embodiments described above produce a body of spatio-spectral data, which may be used in biometrics applications as described below. The invention is not limited to any particular manner of storing or analyzing the body of spatio-spectral data. For purposes of illustration, it is shown in the form of a datacube in FIG. 5. The datacube 501 is shown decomposed along a spectral dimension with a plurality of planes 503, 505, 507, 509, 511, each of which corresponds to a different portion of the light spectrum and each of which include spatial information. In some instances, the body of spatio-spectral data may include additional types of information beyond spatial and spectral information. For instance, different illumination conditions as defined by different illumination structures, different polarizations, and the like may provide additional dimensions of information. More broadly, data collected under a plurality of optical conditions, whether they be collected simultaneously or sequentially, is referred to herein as "multispectral" data. A more complete description of aspects of multispectral data is described in copending, commonly assigned U.S. patent application Ser. No. 11/379,945, entitled "MULTISPECTRAL BIOMETRIC SENSORS," filed Apr. 24, 2006, the entire disclosure of which is incorporated herein by reference for all purposes. Spatio-spectral data may thus be considered to be a subset of certain types of multispectral data where the different optical conditions include different illumination wavelengths.

In an embodiment where illumination takes place under white light, the images 503, 505, 507, 509, and 511 might correspond, for example to images generated using light at 450 nm, 500 nm, 550 nm, 600 nm, and 650 nm. In another example, there may be three images that correspond to the amount of light in the red, green, and blue spectral bands at each pixel location. Each image represents the optical effects of light of a particular wavelength interacting with skin. Due to the optical properties of skin and skin components that vary by wavelength, each of the multispectral images 503, 505, 507, 509, and 511 will be, in general, different from the others. The datacube may thus be expressed as $R(X_S, Y_S, X_I, Y_I, \lambda)$ and describes the amount of diffusely reflected light of wavelength $\lambda$ seen at each image point $X_I, Y_I$ when illuminated at a source point $X_S, Y_S$. Different illumination configurations (flood, line, etc.) can be summarized by summing the point response over appropriate source point locations. A conventional non-TIR fingerprint image $F(X_I, Y_I)$ can loosely be described as the multispectral data cube for a given wavelength, $\lambda_o$, and summed over all source positions:

$$F(X_I, Y_I) = \sum_{Y_S} \sum_{X_S} R(X_S, Y_S, X_I, Y_I, \lambda_0).$$

Conversely, the spectral biometric dataset $S(\lambda)$ relates the measured light intensity for a given wavelength $\lambda$ to the difference $\vec{D}$ between the illumination and detection locations:

$$S(\vec{D}, \lambda) = R(X_I - X_S, Y_I - Y_S, \lambda).$$

The datacube R is thus related to both conventional fingerprint images and to spectral biometric datasets. The datacube R is a superset of either of the other two data sets and contains correlations and other information that may be lost in either of the two separate modalities.

The light that passes into the skin and/or underlying tissue is generally affected by different optical properties of the skin and/or underlying tissue at different wavelengths. Two optical effects in the skin and/or underlying tissue that are affected differently at different wavelengths are scatter and absorbance. Optical scatter in skin tissue is generally a smooth and relatively slowly varying function wavelength. Conversely, absorbance in skin is generally a strong function of wavelength due to particular absorbance features of certain components present in the skin. For example blood, melanin, water, carotene, biliruben, ethanol, and glucose all have significant absorbance properties in the spectral region from 400 nm to 2.5 μm, which may sometimes be encompassed by the white-light sources.

The combined effect of optical absorbance and scatter causes different illumination wavelengths to penetrate the skin to different depths. This effectively causes the different spectral images to have different and complementary information corresponding to different volumes of illuminated tissue. In particular, the capillary layers close to the surface of the skin have distinct spatial characteristics that can be imaged at wavelengths where blood is strongly absorbing. Because of the complex wavelength-dependent properties of skin and underlying tissue, the set of spectral values corresponding to a given image location has spectral characteristics that are well-defined and distinct. These spectral characteristics may be used to classify the collected image on a pixel-by-pixel basis. This assessment may be performed by generating typical tissue spectral qualities from a set of qualified images. For example, the spatio-spectral data shown in FIG. 5 may be reordered as an N×5 matrix, where N is the number of image pixels that contain data from living tissue, rather than from a surrounding region of air. An eigenanalysis or other factor analysis performed on this set matrix produces the representative spectral features of these tissue pixels. The spectra of pixels in a later data set may then be compared to such previously established spectral features using metrics such as Mahalanobis distance and spectral residuals. If more than a small number of image pixels have spectral qualities that are inconsistent with living tissue, then the sample is deemed to be non-genuine and rejected, thus providing a mechanism for incorporating antispoofing methods in the sensor based on determinations of the liveness of the sample.

Alternatively, textural characteristics of the skin may alone or in conjunction with the spectral characteristics be used to determine the authenticity of the sample. For example, each spectral image may be analyzed in such a way that the magnitude of various spatial characteristics may be described. Methods for doing so include wavelet transforms, Fourier transforms, cosine transforms, gray-level co-occurrence, and the like. The resulting coefficients from any such transform described an aspect of the texture of the image from which they were derived. The set of such coefficients derived from a set of spectral images thus results in a description of the chromatic textural characteristics of the multispectral data. These characteristics may then be compared to similar characteristics of known samples to perform a biometric determination such as spoof or liveness determination. Methods for performing such determinations are generally similar to the methods described for the spectral characteristics above. Applicable classification techniques for such determinations include linear and quadratic discriminant analysis, classification trees, neural networks, and other methods known to those familiar in the art.

Similarly, in an embodiment where the sample is a volar surface of a hand or finger, the image pixels may be classified as "ridge," "valley," or "other" based on their spectral qualities or their chromatic textural qualities. This classification can be performed using discriminant analysis methods such as linear discriminant analysis, quadratic discriminant analysis, principal component analysis, neural networks, and others known to those of skill in the art. Since ridge and valley pixels are contiguous on a typical volar surface, in some instances, data from the local neighborhood around the image pixel of interest are used to classify the image pixel. In this way, a conventional fingerprint image may be extracted for further processing and biometric assessment. The "other" category may indicate image pixels that have spectral qualities that are different than anticipated in a genuine sample. A threshold on the total number of pixels in an image classified as "other" may be set. If this threshold is exceeded, the sample may be determined to be non-genuine and appropriate indications made and actions taken.

In a similar way, multispectral data collected from regions such as the volar surface of fingers may be analyzed to directly estimate the locations of "minutiae points," which are defined as the locations at which ridges end, bifurcate, or undergo other such topographic change. For example, the chromatic textural qualities of the multispectral dataset may be determined in the manner described above. These qualities may then be used to classify each image location as "ridge ending," "ridge bifurcation," or "other" in the manner described previously. In this way, minutiae feature extraction may be accomplished directly from the multispectral data without having to perform computationally laborious calculations such as image normalization, image binarization, image thinning, and minutiae filtering, techniques that are known to those familiar in the art.

Biometric determinations of identity may be made using the entire body of spatio-spectral data or using particular portions thereof. For example, appropriate spatial filters may be applied to separate out the lower spatial frequency information that is typically representative of deeper spectrally active structures in the tissue. The fingerprint data may be extracted using similar spatial frequency separation and/or the pixel-classification methods disclosed above. The spectral information can be separated from the active portion of the image in the manner discussed above. These three portions of the body of spatio-spectral data may then be processed and compared to the corresponding enrollment data using methods known to one familiar in the art to determine the degree of match. Based upon the strength of match of these characteristics, a decision can be made regarding the match of the sample with the enrolled data. Additional details regarding certain types of spatio-spectral analyses that may be performed are provided in U.S. patent application Ser. No. 10/818,698, entitled "MULTISPECTRAL BIOMETRIC SENSOR," filed Apr. 5, 2004 by Robert K. Rowe et al., the entire disclosure of which is incorporated herein by reference for all purposes.

As previously noted, certain substances that may be present in the skin and underlying tissue have distinct absorbance characteristics. For example, ethanol has characteristic absorbance peaks at approximately 2.26 µm, 2.30 µm, and 2.35 µm, and spectral troughs at 2.23 µm, 2.28 µm, 2.32 µm, and 2.38 µm. In some embodiments, noninvasive optical measurements are performed at wavelengths in the range of 2.1-2.5 µm, more particularly in the range of 2.2-2.4 µm. In an embodiment that includes at least one of the peak wavelengths and one of the trough wavelengths, the resulting spectral data are analyzed using multivariate techniques such as partial least squares, principal-component regression, and others known to those of skill in the art, to provide an estimate of the concentration of alcohol in the tissue, as well as to provide a biometric signature of the person being tested. While a correlation to blood-alcohol level may be made with values determined for a subset of these wavelengths, it is preferable to test at least the three spectral peak values, with more accurate results being obtained when the seven spectral peak and trough values are measured.

In other embodiments, noninvasive optical measurements are performed at wavelengths in the range of 1.5-1.9 µm, more particularly in the range of 1.6-1.8 µm. In specific embodiments, optical measurements are performed at one or more wavelengths of approximately 1.67 µm, 1.69 µm, 1.71 µm, 1.73 µm, 1.74 µm 1.76 µm and 1.78 µm. The presence of alcohol is characterized at these wavelengths by spectral peaks at 1.69 µm, 1.73 µm, and 1.76 µm and by spectral troughs at 1.67 µm, 1.71 µm, 1.74 µm, and 1.78 µm. Similar to the 2.1-2.5 µm wavelength range, the concentration of alcohol is characterized by relative strengths of one or more of the spectral peak and trough values. Also, while a correlation to blood-alcohol level may be made with values determined for a subset of these wavelengths in the 1.5-1.9 µm range, it is preferable to test at least the three spectral peak values, with more accurate results being obtained when the seven spectral peak and trough values are measured.

A small spectral alcohol-monitoring device may be embedded in a variety of systems and applications in certain embodiments. The spectral alcohol-monitoring device can be configured as a dedicated system such as may be provided to law-enforcement personnel, or may be integrated as part of an electronic device such as an electronic fob, wristwatch, cellular telephone, PDA, or any other electronic device, for an individual's personal use. Such devices may include mechanisms for indicating to an individual whether his blood-alcohol level is within defined limits. For instance, the device may include red and green LEDs, with electronics in the device illuminating the green LED if the individual's blood-alcohol level is within defined limits and illuminating the red LED if it is not. In one embodiment, the alcohol-monitoring device may be included in a motor vehicle, typically positioned so that an individual may conveniently place tissue, such as a fingertip, on the device. While in some instances, the device may function only as an informational guide indicating acceptability to drive, in other instances ignition of the motor vehicle may affirmatively depend on there being a determination that the individual has a blood-alcohol level less than a prescribed level.

3. Contact Biometric Sensors

Biometric sensors may be constructed in a fashion similar to that shown in FIGS. 1 and 3, but configured so that the skin site is placed in contact with a platen. Such designs have certain additional characteristics that result from the interaction of light with the platen, sometimes permitting additional information to be incorporated as part of the collect spatio-spectral data.

Figure 6:
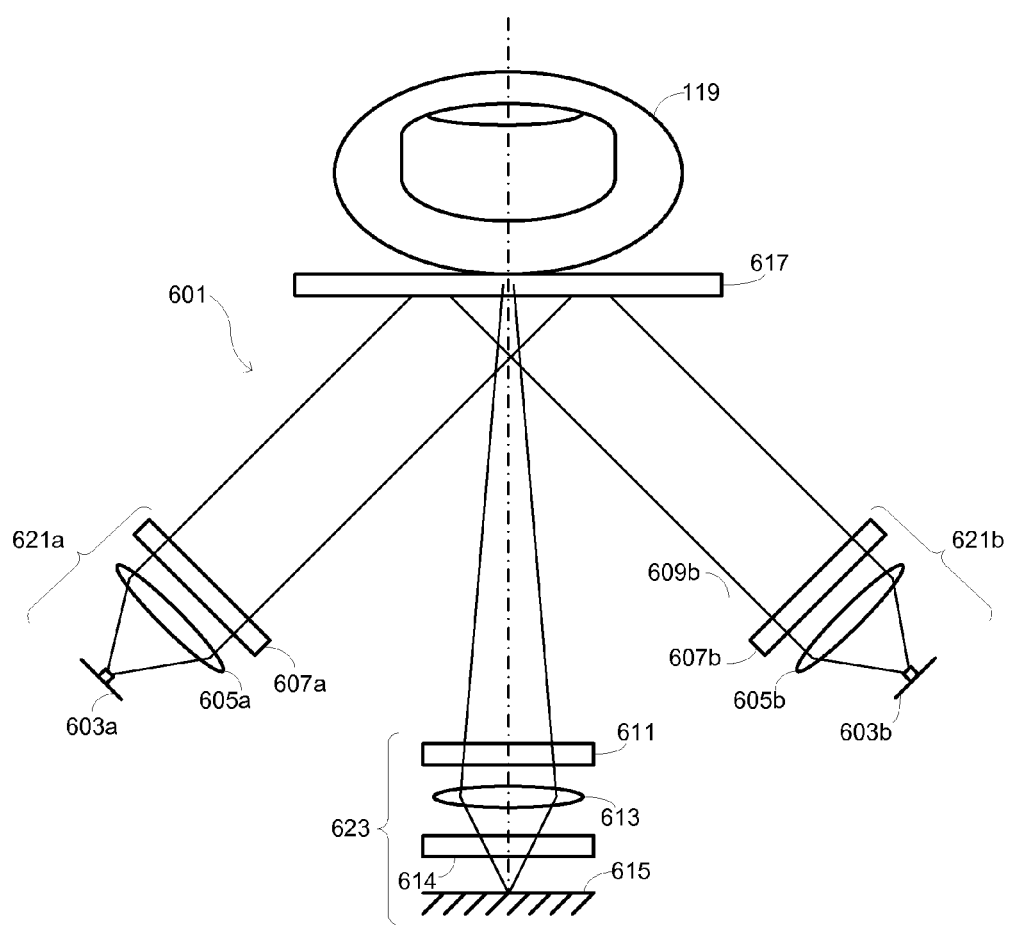
FIG. 6 is a front view of a contact biometric sensor in one embodiment of the invention.

One embodiment is shown in FIG. 6, which provides a front view of a contact biometric sensor 601. Like the sensor illustrated in FIG. 1, the contact sensor 601 has one or more illumination subsystems 621 and a detection subsystem 623. Each of the illumination subsystems 621 comprises one or more white-light sources 603 and illumination optics that shape the light provided by the sources 603 into a desired form. As with the non-contact arrangements, the illumination optics may generally include any combination of optical elements and may sometimes include a scanner mechanism. In some instances, the illumination light is provided as polarized light by disposing a polarizer 607 through which the illumination light passes. Examples of white-light sources 603, including broad- and narrow-band sources were described above, and the sources 603 may be configured to provide sources having different shapes in different embodiments.

The illumination light is directed by the illumination optics 621 to pass through a platen 617 and illuminate the skin site 119. The sensor layout 601 and components may advantageously be selected to minimize the direct reflection of the illumination optics 621. In one embodiment, such direct reflections are reduced by relatively orienting the illumination subsystem 621 and detection subsystem 623 such that the amount of directly reflected light detected is minimized. For instance, optical axes of the illumination subsystem 621 and the detection subsystem 623 may be placed at angles such that a mirror placed on the platen 617 does not direct an appreciable amount of illumination light into the detection subsystem 623. In addition, the optical axes of the illumination and detection subsystems 621 and 623 may be placed at angles relative to the platen 617 such that the angular acceptance of both subsystems is less than the critical angle of the system 601; such a configuration avoids appreciable effects due to total internal reflectance between the platen 617 and the skin site 119.

The presence of the platen 617 does not adversely interfere with the ability to reduce the directly reflected light by use of polarizers. The detection subsystem 623 may include a polarizer 611 having an optical axis substantially orthogonal or parallel to the polarizer 607 comprised by the illumination subsystem 621. Surface reflections at the interface between the platen 617 and the skin site 119 are reduced in the case where polarizers 611 and 607 are oriented substantially orthogonal to each other since light from the sample must undergo sufficiently many scattering events to change its state of polarization before it can be sensed by the detector 615. The detection subsystem 623 may additionally incorporate detection optics that form an image of the region near the platen surface 617 onto the detector 615. In one embodiment, the detection optics 613 comprise a scanning mechanism (not shown) to relay portions of the platen region onto the detector 615 in sequence. An infrared filter 614 may be included to reduce the amount of infrared light detected, particularly in embodiments where the detector 615 is sensitive to infrared light, such as when a Bayer filter array is used. Conversely, as described above, the infrared filter 614 may be omitted in some embodiments and an additional light source 603 with emissions in the infrared may be included in some embodiments.

As in the other arrangements described above, the detection subsystem 623 is generally configured to be sensitive to light that has penetrated the surface of the skin and undergone optical scattering within the skin and/or underlying tissue. The polarizers may sometimes be used to create or accentuate the surface features. For instance, if the illumination light is polarized in a direction parallel ("P") with the platen 617, and the detection subsystem 623 incorporates a polarizer 611 in a perpendicular orientation ("S"), then the reflected light is blocked by as much as the extinction ratio of the polarizer pair. However, light that crosses into the skin site at a ridge point is optically scattered, which effectively randomizes the polarization (though the skin does have some characteristic polarization qualities of its own, as is known to those of skill in the art). This allows a portion, on the order of 50%, of the absorbed and re-emitted light to be observed by the S-polarized imaging system.

Figure 7A:
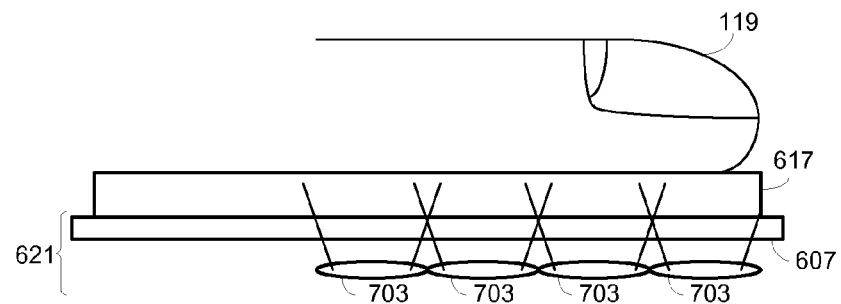
FIG. 7A provides a side view of a contact biometric sensor in an embodiment.

A side view of one of the embodiments of the invention is shown with the schematic drawing provided in FIG. 7A. For clarity, this view does not show the detection subsystem, but does show an illumination subsystem 621 explicitly. The illumination subsystem 621 in this embodiment has a plurality of white-light sources 703 that are distributed spatially. As shown in the drawing, the illumination optics 621 are configured to provide flood illumination, but in alternative embodiments could be arranged to provide line, point, or other patterned illumination by incorporation of cylindrical optics, focusing optics, or other optical components as known to those knowledgeable in the art.

Figure 7B:
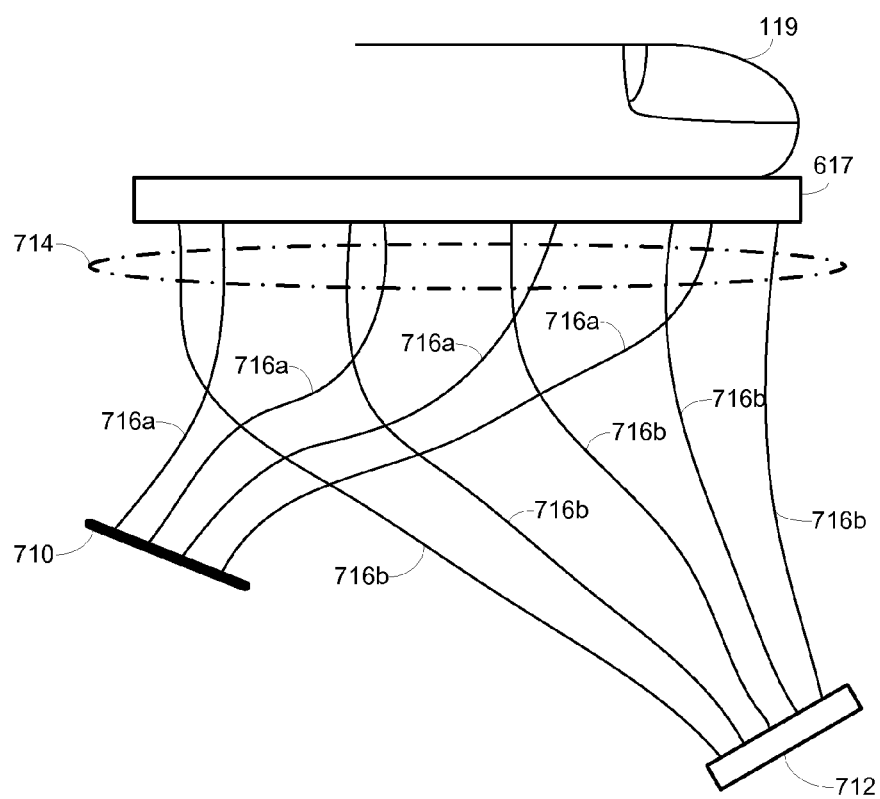
FIG. 7B provides a side view of a contact biometric sensor in another embodiment.

The array of white-light sources 703 in FIG. 7A need not actually be planar as shown in the drawing. For example, in other embodiments, optical fibers, fiber bundles, or fiber optical faceplates or tapers could convey the light from the light sources at some convenient locations to an illumination plane, where light is reimaged onto the skin site 119. The light sources could be controlled turning the drive currents on and off as LEDs might be. Alternatively, if an incandescent source is used, switching of the light may be accomplished using some form of spatial light modulator such as a liquid crystal modulator or using microelectromechanical-systems ("MEMS") technology to control apertures, mirrors, or other such optical elements. Such configurations may allow the structure of the sensor to be simplified. One embodiment is illustrated in FIG. 7B, which shows the use of optical fibers and electronic scanning of illumination sources such as LEDs. Individual fibers 716a connect each of the LEDs located at an illumination array 710 to an imaging surface, and other fibers 716b relay the reflected light back to the imaging device 712, which may comprise a photodiode array, CMOS array, or CCD array. The set of fibers 716a and 716b thus defines an optical fiber bundle 714 used in relaying light.

Figure 8:
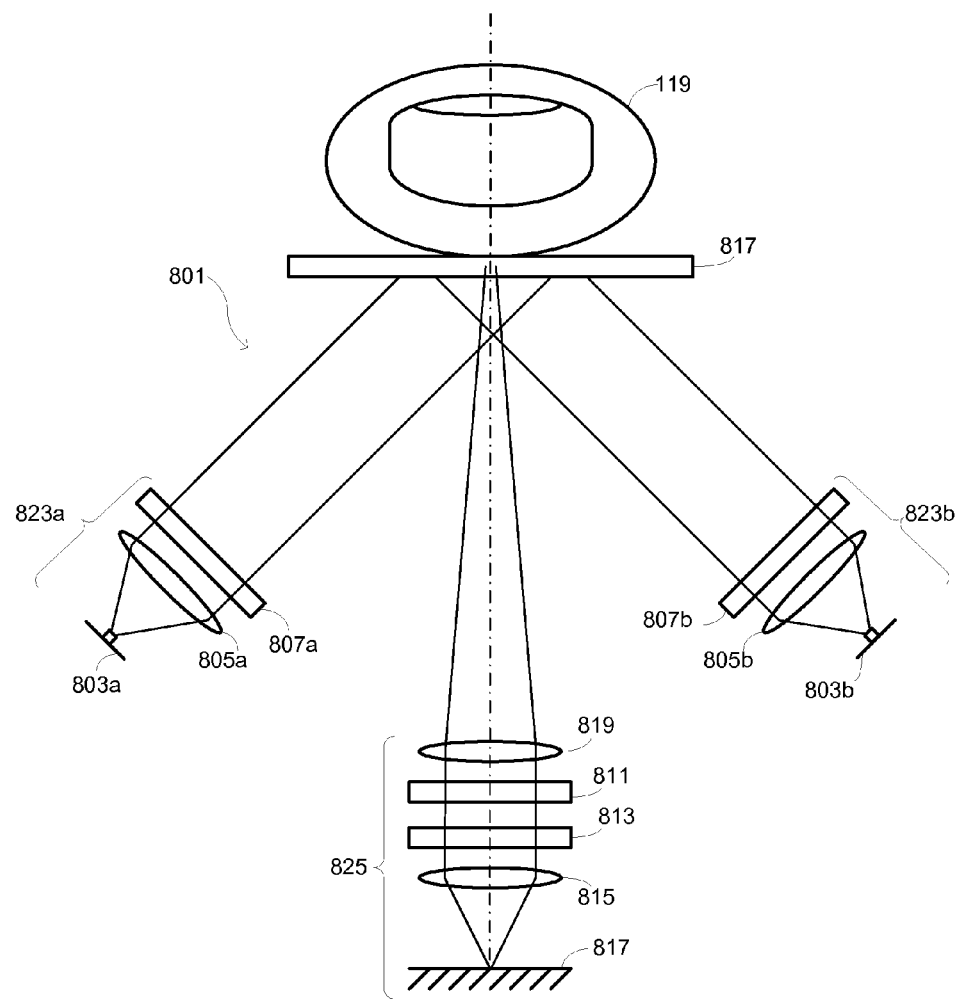
FIG. 8 provides a front view of a contact biometric sensor in a further embodiment of the invention.

Another embodiment of a contact biometric sensor is shown schematically with the front view of FIG. 8. In this embodiment, the biometric sensor 801 comprises one or more white-light illumination subsystems 823 and a detection subsystem 825. The illumination subsystems 823 comprise a white-light source 803 that provides light that passes through illumination optics 805 and a polarizer 807 to be directed to a platen 817 over which a skin site is disposed 119. A portion of the light is diffusely reflected from the skin site 119 into the detection subsystem 825, which comprises imaging optics 815 and 819, a crossed polarizer 811, and a dispersive optical element 813. The first imaging optics 819 collimate light reflected from the skin site 119 for transmission through the crossed polarizer 811 and dispersive element 813. Separated spectral components are separately focused onto the detector 817 by the second imaging optics 815.

Contact biometric sensors like those illustrated in FIGS. 6-8 are also amenable to configurations in which the illumination region is in relative motion with the skin site. As previously noted, such relative motion may be implemented with a mechanism for scanning the illumination light and/or by moving the skin site. The presence of a platen in contact-sensor embodiments generally facilitates motion of the skin site by confining a surface of the skin site to a defined plane; in embodiments where freedom of motion is permitted in three dimensions, additional difficulties may result from movement of the skin site outside the imaging depth. A swipe sensor may accordingly be implemented with contact biometric sensors in a fashion as generally described in connection with FIG. 4 above, but with a platen that prevents motion of the skin site in one direction. While in some embodiments, the swipe sensor may be a stationary system, a contact configuration allows a roller system to be implemented in which the skin site is rolled over a roller structure that is transparent to the white light. An encoder may record position information and aid in stitching a full two-dimensional image from a resulting series of image slices, as understood by those of skill in the art. Light received from discrete portions of the skin site is used to build up the image.

While the above descriptions of noncontact and contact biometric sensors have focused on embodiments in which white light is used, other embodiments may make use of other spectral combinations of light in similar structural arrangements. In addition, other embodiments may include additional variations in optical conditions to provide multispectral conditions. Some description of such multispectral applications is provided in commonly assigned U.S. patent application Ser. No. 10/818,698, entitled "MULTISPECTRAL BIOMETRIC SENSOR," filed Apr. 5, 2004 by Robert K. Rowe et al.; U.S. patent Ser. No. 11/177,817, entitled "LIVENESS SENSOR," filed Jul. 8, 2005 by Robert K. Rowe; U.S. Prov. Pat. No. 60/576,364, entitled "MULTISPECTRAL FINGER RECOGNITION," filed Jun. 1, 2004 by Robert K. Rowe and Stephen P. Corcoran; U.S. Prov. Pat. Appl. No. 60/600,867, entitled "MULTISPECTRAL IMAGING BIOMETRIC," filed Aug. 11, 2004 by Robert K. Rowe; U.S. patent Ser. No. 11/115,100, entitled "MULTISPECTRAL IMAGING BIOMETRICS," filed Apr. 25, 2005 by Robert K. Rowe; U.S. patent application Ser. No. 11/115,101, entitled "MULTISPECTRAL BIOMETRIC IMAGING," filed Apr. 25, 2005; U.S. patent Ser. No. 11/115,075, entitled "MULTISPECTRAL LIVENESS DETERMINATION," filed Apr. 25, 2005; U.S. Prov. Pat. Appl. No. 60/659,024, entitled "MULTISPECTRAL IMAGING OF THE FINGER FOR BIOMETRICS," filed Mar. 4, 2005 by Robert K. Rowe et al.; U.S. Prov. Pat. Appl. No. 60/675,776, entitled "MULTISPECTRAL BIOMETRIC SENSORS," filed Apr. 27, 2005 by Robert K. Rowe; and U.S. patent application Ser. No. 11/379,945, entitled "MULTISPECTRAL BIOMETRIC SENSORS," filed Apr. 24, 2006 by Robert K. Rowe. The entire disclosure of each of the foregoing applications is incorporated herein by reference for all purposes.

The noncontact and contact biometric sensors described above use white-light imaging in certain embodiments. The use of white light permits images to be collected simultaneously at multiple colors, with the overall speed of data collection being faster than in embodiments where discrete states are collected separately. This reduced data-collection time leads to a reduction in motion artifacts as the skin site moves during data collection. The overall sensor size may also be reduced and provided at lower cost by using a smaller number of light sources when compared with the use of discrete illumination sources for different colors. Corresponding reductions are also possible in the electronics used to support coordinated operation of the light sources. In addition, color imagers are currently available at prices that are typically lower than monochrome imagers.

The use of white-light imaging also permits a reduction in data volume when the sensor is designed to use all pixels in achieving the desired resolution. For instance, a typical design criterion may provide a 1-inch field with a 500 dots-per-inch resolution. This can be achieved with a monochrome camera having 500×500 pixels. It can also be achieved with a 1000×1000 color camera when extracting each color plane separately. The same resolution can be achieved by using a 500×500 color imager and converting to {R, G, B} triplets and then extracting the monochrome portion of the image. This is a specific example of a more general procedure in which a color imager is used by converting to primary-color triplets, followed by extraction of a monochrome portion of an image. Such a procedure generally permits a desired resolution to be achieved more efficiently than with other extraction techniques.

4. Texture Biometric Sensor

Another form of contact biometric sensor provided in embodiments of the invention is a texture biometric sensor. "Image texture" refers generally to any of a large number of metrics that describe some aspect of a spatial distribution of tonal characteristics of an image, some of which were described above. For example, some textures, such as those commonly found in fingerprint patterns or wood grain, are flowlike and may be well described by metrics such as an orientation and coherence. For textures that have a spatial regularity (at least locally), certain characteristics of the Fourier transform and the associated power spectrum are important such as energy compactness, dominant frequencies and orientations, etc. Certain statistical moments such as mean, variance, skew, and kurtosis may be used to describe texture. Moment invariants may be used, which are combinations of various moments that are invariant to changes in scale, rotation, and other perturbations. Gray-tone spatial dependence matrices may be generated and analyzed to describe image texture. The entropy over an image region may be calculated as a measure of image texture. Various types of wavelet transforms may be used to describe aspects of the image texture. Steerable pyramids, Gabor filters, and other mechanisms of using spatially bounded basis functions may be used to describe the image texture. These and other such measures of texture known to one familiar in the art may be used individually or in combination in embodiments of the invention.

Image texture may thus be manifested by variations in pixel intensities across an image, which may be used in embodiments of the invention to perform biometric functions. In some embodiments, additional information may be extracted when such textural analysis is performed for different spectral images extracted from a multispectral data set, producing a chromatic textural description of the skin site. These embodiments advantageously enable biometric functions to be performed by capturing a portion of an image of a skin site. The texture characteristics of the skin site are expected to be approximately consistent over the skin site, permitting biometric functions to be performed with measurements made at different portions of the image site. In many instances, it is not even required that the portions of the skin site used in different measurements overlap with each other.

This ability to use different portions of the skin site provides considerable flexibility in the structural designs that may be used. This is, in part, a consequence of the fact that biometric matching may be performed statistically instead of requiring a match to a deterministic spatial pattern. The sensor may be configured in a compact manner because it need not acquire an image over a specified spatial area. The ability to provide a small sensor also permits the sensor to be made more economically than sensors that need to collect complete spatial information to perform a biometric function. In different embodiments, biometric functions may be performed with purely spectral information, while in other embodiments, spatio-spectral information is used.

Figure 9A:
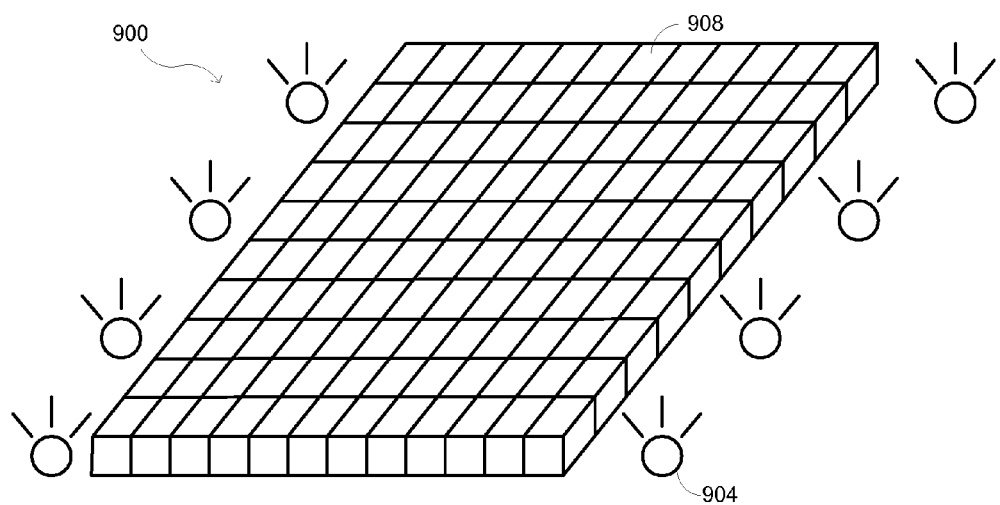
FIG. 9A illustrates a structure for a contact texture biometric sensor in an embodiment of the invention.

One example of a structure for a texture biometric sensor is shown schematically in FIG. 9A. The sensor 900 comprises a plurality of light sources 904 and an imager 908. In some embodiments, the light sources 904 comprise white-light sources, although in other embodiments, the light sources comprise quasimonochromatic sources. Similarly, the imager 908 may comprise a monochromatic or color imager, one example of which is an imager having a Bayer pattern. The sensor 900 is referred to herein as a "contact" sensor because the image is collected substantially in the plane of the skin site 119 being measured. It is possible, however, to have different configurations for operating the sensor, some with the imager 908 substantially in contact with the skin site 119 and some with the imager 908 displaced from the plane of the skin site 119.

Figure 9B:
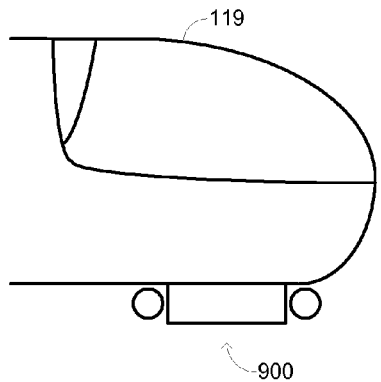
FIG. 9B provides a side view of a contact texture biometric sensor in one configuration.
Figure 9C:
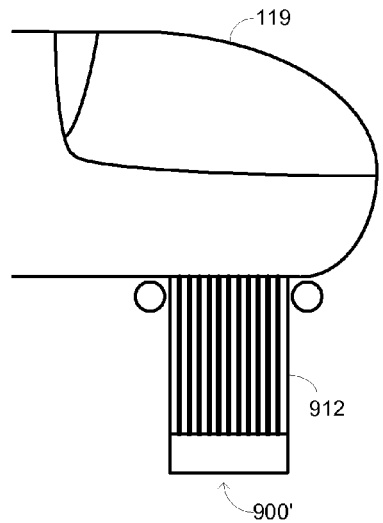
FIG. 9C provides a side view of a contact texture biometric sensor in another configuration.

This is shown for two illustrative embodiments in FIGS. 9B and 9C. In the embodiment of FIG. 9B, the imager 908 is substantially in contact with the skin site 119. Light from the sources 904 propagates beneath the tissue of the skin site 119, permitting light scattered from the skin site 119 and in the underlying tissue to be detected by the imager 908. An alternative embodiment in which the imager 908 is displaced from the skin site 119 is shown schematically in FIG. 9C. In this drawing the sensor 900' includes an optical arrangement 912 that translates an image at the plane of the skin site 119 to the imager could comprise a plurality of optical fibers, which translate individual pixels of an image by total internal reflection along the fiber without substantially loss of intensity. In this way, the light pattern detected by the imager 908 is substantially the same as the light pattern formed at the plane of the skin site 119. The sensor 900' may thus operate in substantially the same fashion as the sensor 900 shown in FIG. 9B. That is, light from the sources 904 is propagated to the skin site, where it is reflected and scattered by underlying tissue after penetrating the skin site 119. Because information is merely translated substantially without loss, the image formed by the imager 908 in such an embodiment is substantially identical to the image that would be formed with an arrangement like that in FIG. 9A.

In embodiments where purely spectral information is used to perform a biometric function, spectral characteristics in the received data are identified and compared with an enrollment database of spectra. The resultant tissue spectrum of a particular individual includes unique spectral features and combinations of spectral features that can be used to identify individuals once a device has been trained to extract the relevant spectral features. Extraction of relevant spectral features may be performed with a number of different techniques, including discriminant analysis techniques. While not readily apparent in visual analysis of a spectral output, such analytical techniques can repeatably extract unique features that can be discriminated to perform a biometric function. Examples of specific techniques are disclosed in commonly assigned U.S. Pat. No. 6,560,352, entitled "APPARATUS AND METHOD OF BIOMETRIC IDENTIFICATION AND VERIFICATION OF INDIVIDUALS USING OPTICAL SPECTROSCOPY"; U.S. Pat. No. 6,816,605, entitled "METHODS AND SYSTEMS FOR BIOMETRIC IDENTIFICATION OF INDIVIDUALS USING LINEAR OPTICAL SPECTROSCOPY"; U.S. Pat. No. 6,628,809, entitled "APPARATUS AND METHOD FOR IDENTIFICATION OF INDIVIDUALS BY NEAR-INFRARED SPECTROSCOPY"; U.S. patent application Ser. No. 10/660,884, entitled "APPARATUS AND METHOD FOR IDENTIFICATION OF INDIVIDUAL BY NEAR-INFRARED SPECTROSCOPY," filed Sep. 12, 2003 by Robert K. Rowe et al.; and U.S. patent application Ser. No. 09/874,740, entitled "APPARATUS AND METHOD OF BIOMETRIC DETERMINATION USING SPECIALIZED OPTICAL SPECTROSCOPY SYSTEM," filed Jun. 5, 2001 by Robert K. Rowe et al. The entire disclosure of each of the foregoing patents and patent applications is incorporated herein by reference in its entirety.

The ability to perform biometric functions with image-texture information, including biometric identifications, may exploit the fact that a significant portion of the signal from a living body is due to capillary blood. For example, when the skin site 119 comprises a finger, a known physiological characteristic is that the capillaries in the finger follow the pattern of the external fingerprint ridge structure. Therefore, the contrast of the fingerprint features relative to the illumination wavelength is related to the spectral features of blood. In particular, the contrast of images taken with wavelengths longer than about 580 nm are significantly reduced relative to those images taken with wavelengths less than about 580 nm. Fingerprint patterns generated with nonblood pigments and other optical effects such as Fresnel reflectance have a different spectral contrast.

Light scattered from a skin site 119 may be subjected to variety of different types of comparative texture analyses in different embodiments. Some embodiments make use of a form of moving-window analysis of image data derived from the collected light to generate a figure of merit, and thereby evaluate the measure of texture or figure of merit. In some embodiments, the moving window operation may be replaced with a block-by-block or tiled analysis. In some embodiments, a single region of the image or the whole image may be analyzed at one time.

In one embodiment, fast-Fourier transforms are performed on one or more regions of the image data. An in-band contrast figure of merit C is generated in such embodiments as the ratio of the average or DC power to in-band power. Specifically, for an index i that corresponds to one of a plurality of wavelengths comprised by the white light, the contrast figure of merit is $$C_i \equiv \frac{\sum_\xi \sum_\eta |F_i(\xi, \eta)|^2 \Big|_{R_{low}^2 < (\xi^2 + \eta^2) < R_{high}^2}}{|F_i(0, 0)|^2}.$$

In this expression, $F_i(\xi,\eta)$ is the Fourier transform of the image $f_i(x,y)$ at the wavelength corresponding to index i, where x and y are spatial coordinates for the image. The range defined by $R_{low}$ and $R_{high}$ represents a limit on spatial frequencies of interest for fingerprint features. For example, $R_{low}$ may be approximately 1.5 fringes/mm in one embodiment and $R_{high}$ may be 3.0 fringes/mm. In an alternative formulation, the contrast figure of merit may be defined as the ratio of the integrated power in two different spatial frequency bands. The equation shown above is a specific case where one of the bands comprises only the DC spatial frequency.

In another embodiment, moving-window means and moving-window standard deviations are calculated for the collected body of data and used to generate the figure of merit. In this embodiment, for each wavelength corresponding to index i, the moving-window mean $\mu_i$ and the moving-window standard deviation $\sigma_i$ are calculated from the collected image $f_i(x, y)$. The moving windows for each calculation may be the same size and may conveniently be chosen to span on the order of 2-3 fingerprint ridges. Preferably, the window size is sufficiently large to remove the fingerprint features but sufficiently small to have background variations persist. The figure of merit $C_i$ in this embodiment is calculated as the ratio of the moving-window standard deviation to the moving-window mean:

$$C_i = \frac{\sigma_i}{\mu_i}.$$

In still another embodiment, a similar process is performed but a moving-window range (i.e., max(image values)-min (image values)) is used instead of a moving-window standard deviation. Thus, similar to the previous embodiment, a moving-window mean $\mu_i$ and a moving-window range $\delta_i$ are calculated from the collected image $f_i(x,y)$ for each wavelength corresponding to index i. The window size for calculation of the moving-window mean is again preferably large enough to remove the fingerprint features but small enough to maintain background variations. In some instances, the window size for calculation of the moving-window mean is the same as for calculation of the moving-window range, a suitable value in one embodiment spanning on the order of 2-3 fingerprint ridges. The figure of merit in this embodiment is calculated as the ratio of the moving-window mean:

$$C_i = \frac{\delta_i}{\mu_i}.$$

This embodiment and the preceding one may be considered to be specific cases of a more general embodiment in which moving-window calculations are performed on the collected data to calculate a moving-window centrality measure and a moving-window variability measure. The specific embodiments illustrate cases in which the centrality measure comprises an unweighted mean, but may more generally comprise any other type of statistical centrality measure such as a weighted mean or median in certain embodiments. Similarly, the specific embodiments illustrate cases in which the variability measure comprises a standard deviation or a range, but may more generally comprise any other type of statistical variability measure such as a median absolute deviation or standard error of the mean in certain embodiments.

In another embodiment that does not use explicit moving-window analysis, a wavelet analysis may be performed on each of the spectral images. In some embodiments, the wavelet analysis may be performed in a way that the resulting coefficients are approximately spatially invariant. This may be accomplished by performing an undecimated wavelet decomposition, applying a dual-tree complex wavelet method, or other methods of the sort. Gabor filters, steerable pyramids and other decompositions of the sort may also be applied to produce similar coefficients. Whatever method of decomposition is chosen, the result is a collection of coefficients that are proportional to the magnitude of the variation corresponding to a particular basis function at a particular position on the image. To perform spoof detection, the wavelet coefficients, or some derived summary thereof, may be compared to the coefficients expected for genuine samples. If the comparison shows that the results are sufficiently close, the sample is deemed authentic. Otherwise, the sample is determined to be a spoof. In a similar manner, the coefficients may also be used for biometric verification by comparing the currently measured set of coefficients to a previously recorded set from the reputedly same person.

5. Exemplary Applications

Figure 10:
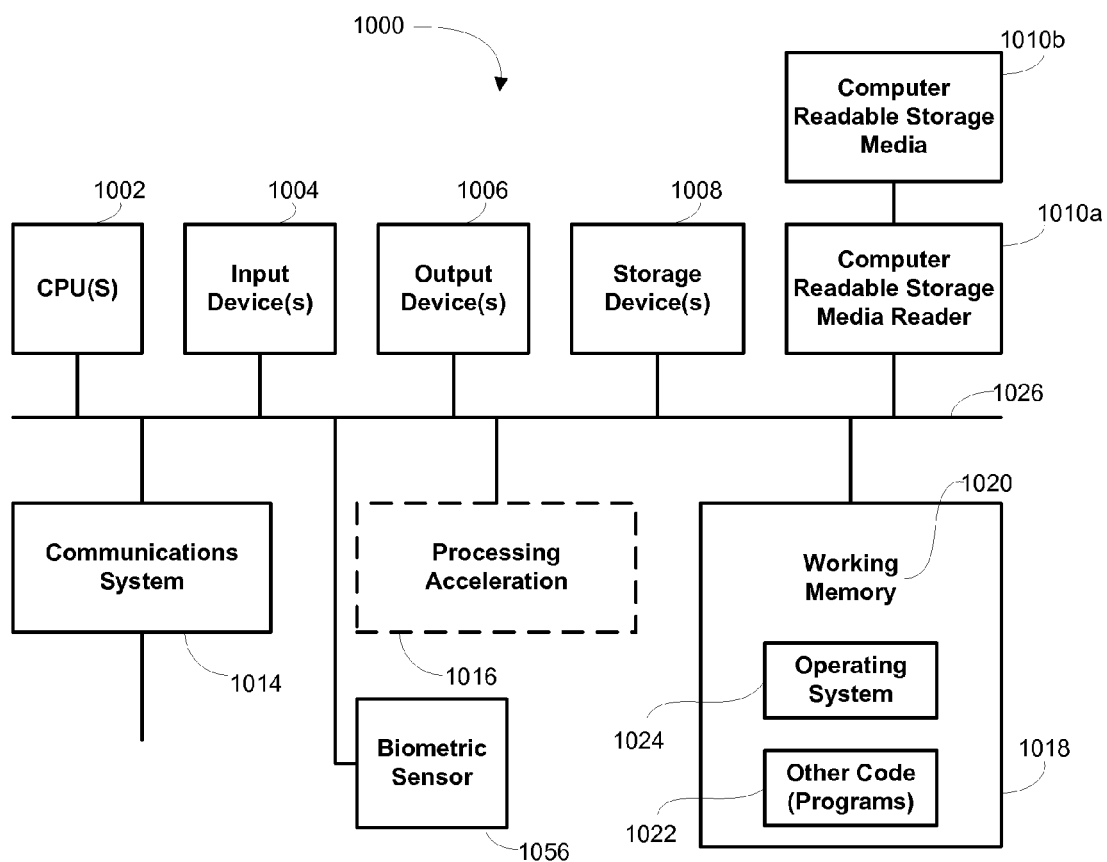
FIG. 10 is schematic representation of a computer system that may be used to manage functionality of contact and noncontact biometric sensors in accordance with embodiments of the invention.

In various embodiments, a biometric sensor, whether it be a noncontact, contact, or texture sensor of any of the types described above, may be operated by a computational system to implement biometric functionality. FIG. 10 broadly illustrates how individual system elements may be implemented in a separated or more integrated manner. The computational device 1000 is shown comprised of hardware elements that are electrically coupled via bus 1026, which is also coupled with the biometric sensor 1056. The hardware elements include a processor 1002, an input device 1004, an output device 1006, a storage device 1008, a computer-readable storage media reader 1010a, a communications system 1014, a processing acceleration unit 1016 such as a DSP or special-purpose processor, and a memory 1018. The computer-readable storage media reader 1010a is further connected to a computer-readable storage medium 1010b, the combination comprehensively representing remote, local, fixed, and/or removable storage devices plus storage media for temporarily and/or more permanently containing computer-readable information. The communications system 1014 may comprise a wired, wireless, modem, and/or other type of interfacing connection and permits data to be exchanged with external devices.

The computational device 1000 also comprises software elements, shown as being currently located within working memory 1020, including an operating system 1024 and other code 1022, such as a program designed to implement methods of the invention. It will be apparent to those skilled in the art that substantial variations may be used in accordance with specific requirements. For example, customized hardware might also be used and/or particular elements might be implemented in hardware, software (including portable software, such as applets), or both. Further, connection to other computing devices such as network input/output devices may be employed.

Figure 11:
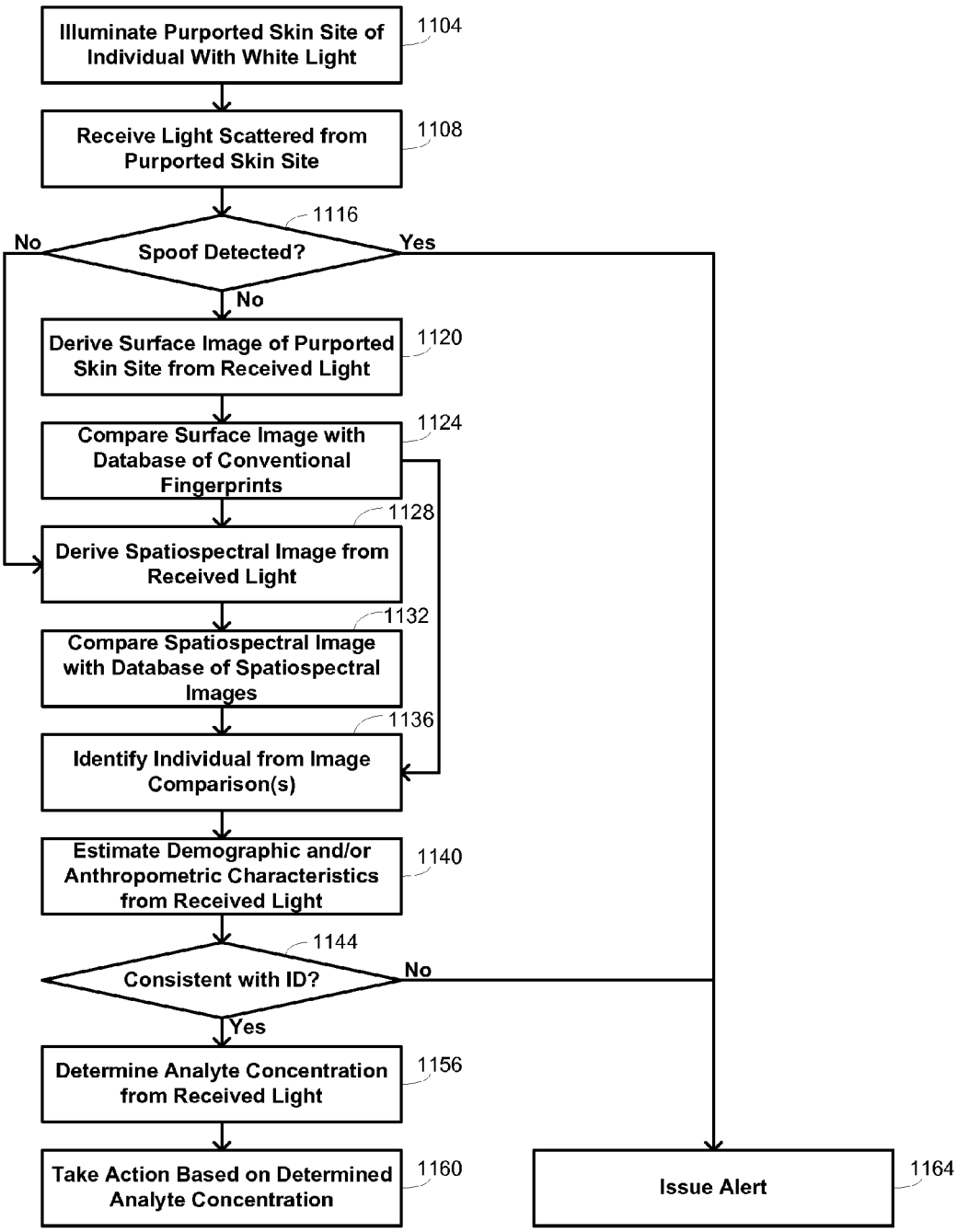
FIG. 11 is a flow diagram summarizing methods of using contact and noncontact biometric sensors and illustrates a number of different biometric functions that may be performed.

An overview of functionality that may be implemented with the computational device are summarized with the flow diagram of FIG. 11. In some embodiments, a purported skin site is illuminated as indicated at block 1104 with white light. This permits the biometric sensor to receive light from the purported skin site at block 1108. As described above, the received light may be analyzed in a number of different ways in implementing a biometric function. The flow diagram shows how certain combinations of analyses may be used in implementing the biometric function, although it is not necessary that all steps be performed. In other instances, a subset of the steps may be performed, additional steps might be performed, and/or the indicated steps might be performed in a different order than indicated.

At block 1112, a liveness check may be performed with the received light to confirm that the purported skin site is not some type of spoof, usually by verifying that it has the characteristics of living tissue. If a spoof is detected, an alert may be issued at block 1164. The specific type of alert that is issued may depend on the environment in which the biometric sensor is deployed, with audible or visual alerts sometimes being issued near the sensor itself; in other instances, silent alerts may be transmitted to security or law-enforcement personnel.

The light received scattered from the purported skin site may be used at block 1120 to derive a surface image of the purported skin site. In instances where the purported skin site is a volar surface of a finger, such a surface image will include a representation of the pattern of ridges and valleys on the finger, permitting it to be compared with a database of conventional fingerprints at block 1124. In addition or alternatively, the received light may be used to derive a spatio-spectral image at block 1128. This image may be compared with a spatio-spectral database having images that are associated with individuals at block 1132. In either instance, the comparison may permit the individual to be identified at block 1136 as a result of the comparison. It is generally expected that higher-reliability identifications may be made by using the full spatio-spectral information to provide a comparison with spatio-spectral images. But in some applications, there may be greater availability of conventional fingerprint data, with some individuals having their fingerprints stored in large law-enforcement fingerprint databases but not in spatio-spectral databases. In such cases, embodiments of the invention advantageously permit the extraction of a conventional fingerprint image to perform the identification.

The spatio-spectral data includes still additional information that may provide greater confidence in the identification, whether the identification is made by comparison with a conventional fingerprint database or through comparison with spatio-spectral information. For example, as indicated at block 1140, demographic and/or anthropometric characteristics may be estimated from the received light. When the database entry matched to the image at block 1136 includes demographic or anthropometric information, a consistency check may be performed at block 1144. For instance, an individual presenting himself may be identified as a white male having an age of 20-35 years from the estimated demographic and anthropometric characteristics. If the database entry against which the image is matched identifies the individual as a 68-year-old black woman, there is a clear inconsistency that would trigger the issuance of an alarm at block 1164.

Other information may also be determined from the received light, such as an analyte concentration at block 1156. Different actions may sometimes be taken in accordance with the determined analyte level. For example, ignition of an automobile might be prohibited if a blood-alcohol level exceeds some threshold, or an alarm might be issued if a blood-glucose level of a medical patient exceeds some threshold. Other physiological parameters, such as skin dryness conditions and the like, may be estimated in other applications, with still other actions sometimes being taken in response.

Figure 12:
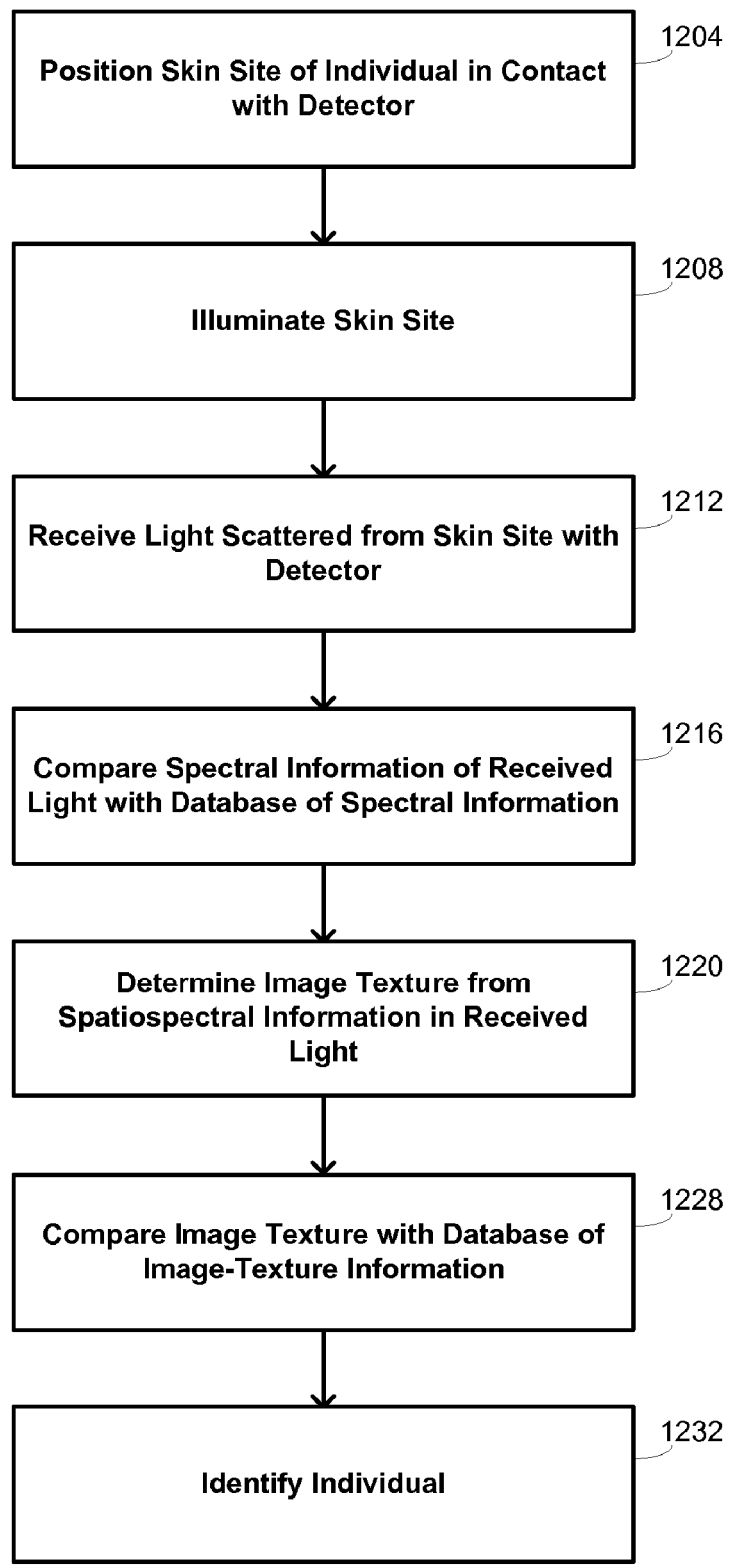
FIG. 12 is a flow diagram summarizing methods of operation of contact texture biometric sensors in accordance with embodiments of the invention.

FIG. 12 provides a similar flow diagram to illustrate applications of a texture biometric sensor. The sensor is used by positioning a skin site of an individual in contact with the detector at block 1204. As previously noted, the detector may be relatively small so that only a portion of a finger surface is positioned in contact with the detector; because of the nature of texture biometrics, variations in the specific portion of the surface placed in contact during different measurements are not detrimental. Data are collected by illuminating the skin site at block 1208 and receiving light scattered from the skin site with the detector at block 1212.

The flow diagram indicates that different types of analyses may be performed. It is not necessary that each of these analyses be performed in every case and, indeed, it is generally expected that in most applications only a single type of analysis will be used. One category of analysis, indicated generally at block 1216, uses purely spectral comparisons of information. Another category of analysis, indicated generally at blocks 1220 and 1228 uses image texture information by determining the image texture from spatio-spectral information in the received light at block 1220 and comparing that image texture with a database of texture biometric information at block 1228. With either or both types of analysis, a biometric function is performed, such as identification of the individual at block 1232.

Thus, having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

What is claimed is:

1. A noncontact biometric system comprising:
an illumination source configured to illuminate a purported skin site of an individual with light having a first polarization condition, wherein the purported skin site is positioned to interact with the polarized light while not being in contact with any solid surface;
a detection subsystem configured to collect light scattered from the purported skin site having a second polarization condition; and
a computational unit interfaced with the detection subsystem configured to:
derive a plurality of spatially distributed images of the purported skin site from the received light, and
analyze the plurality of spatially distributed images to perform a biometric function.

2. The noncontact biometric system according to claim 1, wherein the first polarization condition and the second polarization condition are orthogonal.

3. The noncontact biometric system according to claim 1, wherein the first polarization condition and the second polarization condition are parallel.

4. The noncontact biometric system according to claim 1, wherein the illumination source comprises a polarizer configured to polarize the light according to the first polarization condition.

5. The noncontact biometric system according to claim 1, wherein the detection subsystem comprises a polarizer configured to polarize the light according to the second polarization condition.

6. The noncontact biometric system according to claim 1, wherein the detection subsystem is configured to configured to collect light scattered from the purported skin site having a third polarization condition, wherein the second polarization condition and the third polarization are orthogonal.

7. The noncontact biometric system according to claim 6, wherein the second polarization condition and the first polarization are orthogonal.

8. The noncontact biometric system according to claim 6, wherein the third polarization condition and the first polarization are parallel.

9. A noncontact biometric system comprising:
an illumination source configured to illuminate a purported skin site of an individual;
a first polarizer configured to polarize the light from the illumination source with a first polarization condition prior to illuminating the purported skin site;

a second polarizer configured to polarize the light scattered from the purported skin with a second polarization condition, wherein the second polarization condition is cross-polarized with the first polarization condition;

a third polarizer configured to polarize the light scattered from the purported skin with a third polarization condition, wherein the third polarization condition is parallel-polarized with the first polarization condition;

a detection subsystem configured to collect the polarized light from the purported skin site through the second polarizer and the third polarizer; and a computational unit interfaced with the detection subsystem configured to derive a plurality of spatially distributed images of the purported skin site from the received light, and analyze the plurality of spatially distributed images to perform a biometric function.

10. The noncontact biometric system according to claim 9, wherein the purported skin site is positioned to interact with the polarized light while not being in contact with any solid surface.

11. A noncontact biometric detection method comprising:
illuminating a purported skin site located within a target space with light having a first polarization condition, wherein the purported skin site is positioned to interact with the polarized light while not being in contact with any solid surface;
receiving polarized light scattered from the purported skin site under a second polarization condition;
deriving a plurality of spatially distributed images of the purported skin site from the received polarized light; and
analyzing the plurality of spatially distributed images to perform the biometric function.

12. The noncontact biometric detection method according to claim 11, wherein the plurality of spatially distributed images corresponding to different volumes of illuminated tissue of the individual.

13. A noncontact biometric detection method comprising:
illuminating a purported skin site located within a target space with light having a first polarization condition;
polarizing a portion of the light scattered from the purported skin site under a second polarization condition;
polarizing a portion of the light scattered from the purported skin site under a third polarization condition, wherein the second polarization condition and the third polarization condition are cross-polarized;
deriving a plurality of spatially distributed images of the purported skin site from the polarized light; and
analyzing the plurality of spatially distributed images to perform the biometric function.

14. The noncontact biometric detection method according to claim 13, wherein the second polarization condition and the first polarization condition are cross-polarized.

15. The noncontact biometric detection method according to claim 13, wherein the third polarization condition and the first polarization condition are parallel-polarized.

16. The noncontact biometric detection method according to claim 13, wherein the purported skin site is positioned to interact with the polarized light while not being in contact with any solid surface.

17. The noncontact biometric detection method according to claim 13, wherein the plurality of spatially distributed images corresponding to different volumes of illuminated tissue of the individual.

18. A noncontact biometric sensor comprising:
an illumination subsystem disposed to illuminate a purported skin site of an individual with light, wherein the purported skin site is positioned to interact with the light while not being in contact with any solid surface;
a detection subsystem disposed to receive light scattered from the purported skin site; and
a computational unit interfaced with the detection subsystem and having:
instructions for deriving a plurality of spatially distributed images of the purported skin site from the received light, the plurality of spatially distributed images corresponding to different volumes of illuminated tissue of the individual; and
instructions for analyzing the plurality of spatially distributed images to perform a biometric function.

19. The noncontact biometric sensor according to claim 18, wherein the illumination subsystem is configured to illuminate the purported skin site with white light.

20. The noncontact biometric sensor according to claim 18, wherein detection subsystem comprises a color imager on which the received light is incident.

21. The noncontact biometric sensor according to claim 18, wherein the illumination subsystem is configured to illuminate the purported skin site with polarized light having a first polarization condition; and wherein the detection subsystem comprises a polarizer configured to filter the received light according to a second polarization condition.

22. The noncontact biometric sensor according to claim 21, wherein the first polarization condition and the second polarization condition are cross-polarized relative to one another.

23. The noncontact biometric sensor according to claim 21, wherein the first polarization condition and the second polarization condition are parallel-polarized relative to one another.

24. A method of performing a noncontact biometric function, the method comprising:
illuminating a purported skin site of an individual, wherein the purported skin site is positioned to interact with the polarized light while not being in contact with any solid surface;
receiving light scattered from the purported skin site;
deriving a plurality of spatially distributed images of the purported skin site from the received light; and
analyzing the plurality of spatially distributed images to perform the biometric function.

25. The method according to claim 24, wherein the illuminating the purported skin site of an individual comprises illuminating the skin site of the individual with white light.

26. The method according to claim 24, wherein the plurality of spatially distributed images correspond to different volumes of illuminated tissue of the individual.

* * * * *